United States Patent
Tisdell et al.

(10) Patent No.: US 6,924,298 B2
(45) Date of Patent: Aug. 2, 2005

(54) 2-(3,5-DISUBSTITUTED-4-PYRIDYL)-4-(THIENYL, THIAZOLYL OR ARYLPHENYL)-1,3-OXAZOLINE COMPOUNDS

(75) Inventors: Francis Eugene Tisdell, Carmel, IN (US); Scott Jerome Bis, Midland, MI (US); Vidyadhar Babu Hegde, Carmel, IN (US); Timothy Patrick Martin, Indianapolis, IN (US); Denise Marie Perreault, Indianapolis, IN (US); Maurice Chee Hoong Yap, Zionsville, IN (US); Katherine Anne Guenthenspberger, Daleville, IN (US); James Edwin Dripps, Carmel, IN (US); James Michael Gifford, Lebanon, IN (US); Joe Raymond Schoonover, Ceries, CA (US); Laura Lee Karr, Lebanon, IN (US); Leonard Paul Dintenfass, Indianapolis, IN (US); Paul Allen Neese, Tucson, AZ (US)

(73) Assignee: Dow AgroSciences LLC, Indianapolis, IN (US)

( * ) Notice: Subject to any disclaimer, the term of this patent is extended or adjusted under 35 U.S.C. 154(b) by 78 days.

(21) Appl. No.: 10/297,418

(22) PCT Filed: Jun. 22, 2001

(86) PCT No.: PCT/US01/20135

§ 371 (c)(1),
(2), (4) Date: Apr. 23, 2003

(87) PCT Pub. No.: WO01/98296

PCT Pub. Date: Dec. 27, 2001

(65) Prior Publication Data

US 2004/0006108 A1 Jan. 8, 2004

Related U.S. Application Data

(60) Provisional application No. 60/213,308, filed on Jun. 22, 2000.

(51) Int. Cl.$^7$ ................. A61K 31/443; C07D 413/04
(52) U.S. Cl. ................. 514/340; 514/342; 546/271.1; 546/271.4
(58) Field of Search ................. 514/340, 342; 546/271.4, 271.1, 280.4

(56) References Cited

FOREIGN PATENT DOCUMENTS

| EP | 0345775 | | 12/1989 |
|----|---------|---|---------|
| EP | 0432661 | | 6/1991 |
| EP | 0553623 | | 8/1993 |
| JP | 06145169 | * | 5/1994 |
| JP | 2888946 | | 5/1999 |
| WO | WO 93/24470 | | 12/1993 |
| WO | WO 9622283 | | 7/1996 |
| WO | WO 98/47881 | | 10/1998 |
| WO | WO 99/01443 | | 1/1999 |
| WO | WO 99/23081 | | 5/1999 |
| WO | WO 99/65901 | | 12/1999 |
| WO | WO 00/24735 | | 5/2000 |

* cited by examiner

Primary Examiner—Joseph K. McKane
Assistant Examiner—Janet L Coppins
(74) Attorney, Agent, or Firm—Craig Mixan

(57) ABSTRACT

Oxazoline compounds having a 3,5-disubstituted-4-pyridyl group in the 2-position and a thienyl, thiazolyl or an arylphenyl group in the 4-position are effective in controlling aphids, insects and mites.

5 Claims, No Drawings

150
2-(3,5-DISUBSTITUTED-4-PYRIDYL)-4-(THIENYL, THIAZOLYL OR ARYLPHENYL)-1,3-OXAZOLINE COMPOUNDS

CROSS-REFERENCE TO RELATED APPLICATIONS

This application claims the benefit of U.S. Provisional Application No. 60/213,308, filed Jun. 22, 2000.

BACKGROUND OF THE INVENTION

This invention provides new 2-(4-pyridyl)-oxazoline compounds that are useful as insecticides and acaricides. More particularly, the present invention concerns 2-(3,5-disubstituted-4-pyridyl)-1,3-oxazoline compounds and certain of their stereoisomers. The invention also includes new synthetic procedures and intermediates for preparing the compounds, pesticide compositions containing the compounds, and methods of controlling insects and mites using the compounds.

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore a need exists for new insecticides and acaricides, and particularly for compounds that have new or atypical modes of action.

Certain 3-(3,5-disubstituted-4-pyridyl)-1H-1,2,4-triazoles with activity against mites and insects are disclosed in WO 00/24735. 2-(Substituted-phenyl)-1,3-oxazolines with insecticidal activity are disclosed in JP 4-89484, EP 0345775-A1, EP 0432661-A2, EP 0553623-A1, WO 99/01443, WO 99/23081 and WO 98/47881. 2-Aryl- and 2-heteroaryl-1,3-oxazolines with acaricidal and insecticidal activity are disclosed in JP 6-145169 and WO 99/65901. Arthropocidal 2-(substituted-phenyl)-1,3-oxazolines are disclosed in WO 93/24470. To the applicants' knowledge, only one oxazoline product, etoxazole, has been developed as a commercial acaricide. It would be highly desirable to discover related compounds of this mode of action that are more potent, more selective or of broader spectrum in their activity and/or that have improved toxicological and environmental properties.

SUMMARY OF THE INVENTION

This invention provides novel substituted pyridyl oxazoline derivatives especially useful for the control of insects and mites.

More specifically, the invention provides novel insecticidally active compounds of the formula (I)

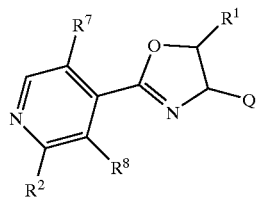

(I)

wherein
$R^1$ represents H, $(C_1-C_6)$ alkyl, $(C_1-C_6)$ haloalkyl, $(C_2-C_6)$ alkenyl, $(C_2-C_6)$ alkynyl, or $(C_1-C_6)$ alkoxyalkyl;

$R^2$ represents H, halogen, $(C_1-C_6)$ alkyl, $(C_1-C_6)$ haloalkyl, $(C_1-C_6)$ alkoxy, $(C_1-C_6)$ haloalkoxy;
Q is a group selected from

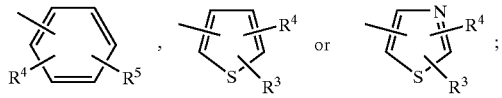

$R^3$ represents H, halogen, $(C_1-C_6)$ alkyl, $(C_7-C_{21})$ straight chain alkyl, hydroxy, $(C_1-C_6)$ alkoxy, $(C_1-C_6)$ haloalkyl, $(C_1-C_6)$ haloalkoxy, $(C_1-C_6)$ alkoxyalkyl, $(C_1-C_6)$ alkoxyalkoxy, $(C_2-C_6)$ alkenyl, $(C_2-C_6)$ haloalkenyl, CN, $NO_2$, $CO_2R^6$, $CON(R^6)_2$, $(C_3-C_6)$ cycloalkyl, $S(O)_m R^6$, SCN, pyridyl, substituted pyridyl, isoxazolyl, substituted isoxazolyl, thienyl, substituted thienyl, thiazolyl, substituted thiazolyl, phenyl, substituted phenyl, $-(CH_2)_n R^6$, $-CH=CHR^6$, $-C\equiv CR^6$, $-CH_2OR^6$, $-CH_2SR^6$, $-CH_2NR^6R^6$, $-OCH_2R^6$, $-SCH_2R^6$, $-NR^6CH_2R^6$,

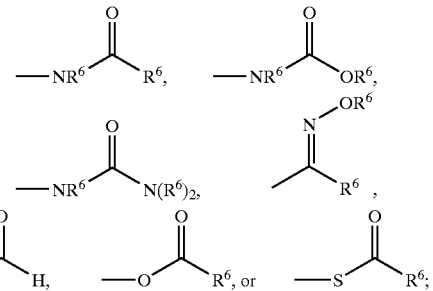

$R^4$ represents H, halogen, $(C_1-C_6)$ alkyl, $(C_1-C_6)$ alkoxy, $(C_1-C_6)$ haloalkyl, $(C_1-C_6)$ haloalkoxy, CN, $CO_2R^6$, $CON(R^6)_2$, $(C_1-C_6)S(O)_m$ alkyl or $(C_1-C_6)S(O)_m$ haloalkyl;
$R^5$ represents

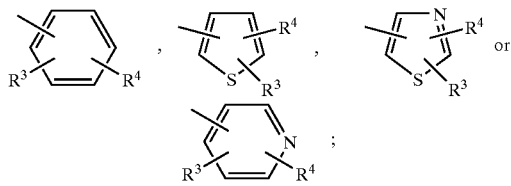

$R^6$ is H, $(C_1-C_6)$ alkyl, $(C_1-C_6)$ haloalkyl, $(C_2-C_6)$ alkenyl, $(C_2-C_6)$ alkynyl, phenyl, or substituted phenyl;
$R^7$ and $R^8$ are independently Cl, F, methyl, halomethyl, methoxy, or halomethoxy;
m is 0, 1, or 2; and
n is 1 or 2;
or a phytologically acceptable acid addition salt or N-oxide thereof.

Preferred compounds of formula (I) include the following classes:

(1) Compounds of formula (I) wherein $R^7$ and $R^8$ are independently F or Cl.
(2) Compounds of formula (I) wherein $R^7$ and $R^8$ are both F or both Cl.
(3) Compounds of formula (I) wherein $R^1$ is H or methyl.
(4) Compounds of formula (I) wherein $R^2$ is H.
(5) Compounds of formula (I) wherein Q represents a group of the formula

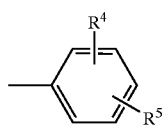

where $R^4$ and $R^5$ are as defined in formula (I).

(6) Compounds of class (5) wherein Q represents a group of the

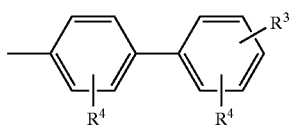

formula
where $R^3$ and $R^4$ are as defined in formula (I).

(7) Compounds of formula (I) wherein $R^3$ and $R^4$ are independently H, halogen, ($C_1$–$C_6$) alkyl, ($C_1$–$C_6$) alkoxy, ($C_1$–$C_6$) haloalkyl or ($C_1$–$C_6$) haloalkoxy.

It will be appreciated by those skilled in the art that the most preferred compounds are generally those which are comprised of various combinations of the above preferred classes.

The invention also provides new processes and intermediates for preparing compounds of formula (I) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

Unless specifically limited otherwise, the terms "alkyl", "alkenyl" and "alkynyl", as well as derivative terms such as "alkoxy" and "alkanoyl", as used herein, include within their scope straight chain, branched chain and cyclic moieties. The terms "alkenyl" and "alkynyl" are intended to include one or more unsaturated bonds.

Unless specifically limited otherwise, the term "halogen", as well as derivative terms such as "halo", as used herein, refers to fluorine, chlorine, bromine, and iodine. Preferred halogens are fluorine and chlorine.

The terms "halomethyl", "haloalkyl", and "haloalkenyl" refer to methyl, alkyl, and alkenyl groups substituted with from one up to the maximum possible number of halogen atoms. The terms "halomethoxy" and "haloalkoxy" refer to methoxy and alkoxy groups substituted with from one up to the maximum possible number of halogen atoms.

The terms "substituted pyridyl," "substituted isoxazolyl," "substituted thienyl," and "substituted thiazolyl" refer to the ring system substituted with one or more groups independently selected from halogen, ($C_1$–$C_4$) alkyl, ($C_1$–$C_4$) haloalkyl, CN, $NO_2$, phenyl, ($C_1$–$C_4$) alkoxy, or ($C_1$–$C_4$) haloalkoxy.

The term "substituted phenyl" refers to a phenyl group substituted with one or more groups independently selected from halogen, ($C_1$–$C_{10}$) alkyl, ($C_1$–$C_7$) haloalkyl, ($C_1$–$C_7$) hydroxyalkyl, ($C_1$–$C_7$) alkoxy, ($C_1$–$C_7$) haloalkoxy, phenoxy, phenyl, $NO_2$, OH, CN, ($C_1$–$C_4$) alkanoyl, benzoyl, ($C_1$–$C_4$) alkanoyloxy, ($C_1$–$C_4$) alkoxycarbonyl, phenoxycarbonyl, or benzoyloxy.

Unless otherwise indicated, when it is stated that a group may be substituted with one or more substituents selected from an identified class, it is intended that the substituents may be independently selected from the class, provided that the substituents are sterically compatible and the rules of chemical bonding and strain energy are satisfied.

When $R^1$ is other than hydrogen, the compounds of this invention can exist as one or more stereoisomers. The various stereoisomers include geometric isomers, diastereomers and enantiomers. Thus the compounds of the present invention include racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

Synthesis

Compounds of formula (I) can be prepared by the method shown in Scheme A:

Scheme A

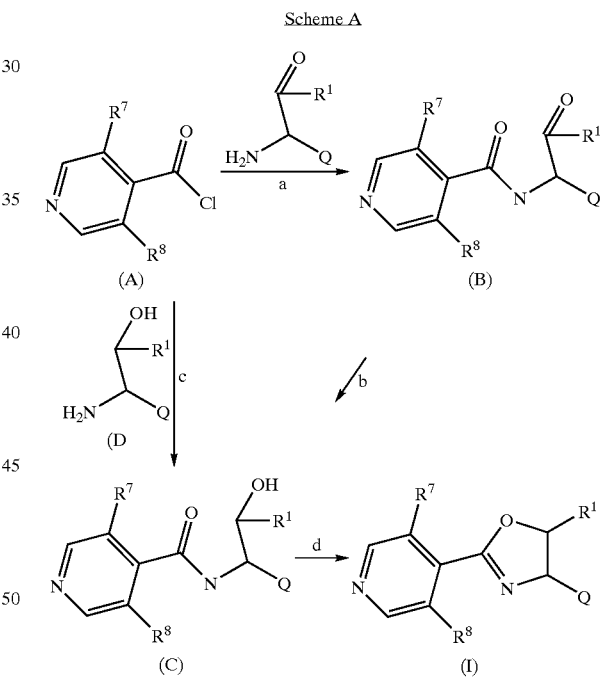

wherein Q, $R^1$, $R^7$ and $R^8$ are as defined in formula (I).

The starting material of formula (A) used in Scheme A can be prepared by reacting the lithium salt of an appropriate isonicotinic acid with thionyl chloride in 1,2-dichloroethane at reflux.

In step a of Scheme A, the compound of formula (A) can be reacted with an aminoacid ester (J. Org. Chem. 1991, 56, 420) to afford a compound of formula (B). 1,2-Dichloroethane is the preferred solvent, however other polar aprotic solvents such as pyridine or THF can also be used.

In step b of Scheme A, the compound of formula (B) can be reacted with a reducing agent such as sodium borohydride to afford a compound of formula (C) in an organic solvent such as ethanol, at a temperature in the range from 0° C. to ambient temperature.

In step c of Scheme A, the compound of formula (A) can be reacted with an aminoalcohol (D) to afford a compound of formula (C). 1,2-Dichloroethane is the preferred solvent, however other polar aprotic solvents such as pyridine or THF can also be used.

In step d of Scheme A, the N-amidealcohol of formula (C) can be reacted with either (diethylamino)sulfur trifluoride (DAST) to provide the product of formula (I) or with thionyl chloride. The ring closure reaction is carried out in dichloromethane, 1,2-dichloroethane or neat at a temperature in the range from −78° C. to ambient temperature.

Alternatively, when Q represents

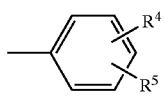

compounds of formula (I) can be prepared by the method shown in Scheme B:

Scheme B

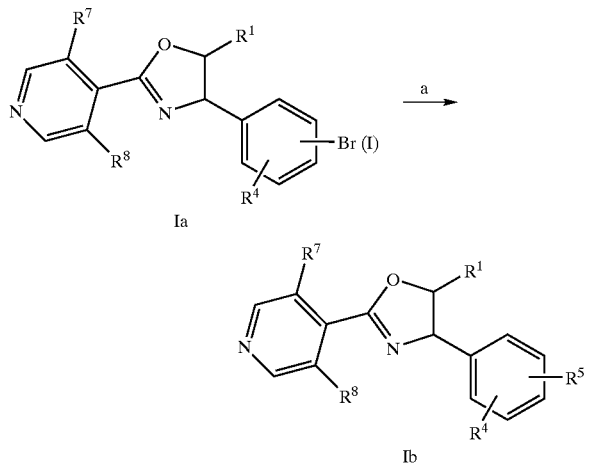

wherein Q, $R^1$, $R^4$, $R^5$, $R^7$ and $R^8$ are as defined in formula (I).

In step a of Scheme B, the oxazoline of formula (Ia) is reacted under standard Suzuki coupling reaction conditions with an appropriately substituted $R^5$-boronic acid to provide the product of formula (Ib). The coupling reaction is carried out in an acetonitrile/water mixture, or ethanol, at a temperature in the range from ambient to refluxing temperature. Catalytic amounts of dichlorobis(triphenylphosphine) palladium(II) or tetrakis(triphenylphosphine)-palladium(0) are typically used for coupling, however other Pd(II) or Pd(0) catalysts can also be used. Typically sodium carbonate is used as base in the coupling reaction but other inorganic or organic bases such as potassium carbonate or triethylamine can also be used.

When $R^1$ does not represent H, compounds of formula (I), in particular diastereomers Syn (I) and Anti (I) can be prepared by the method illustrated in Scheme C:

Scheme C

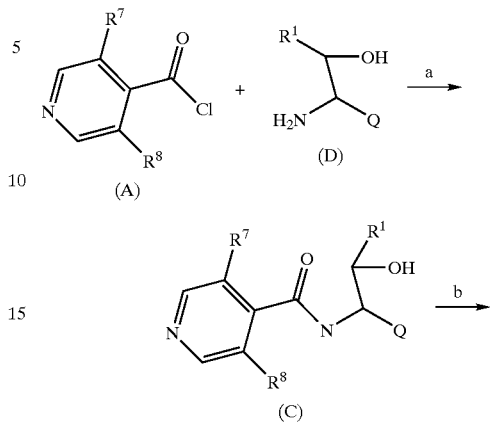

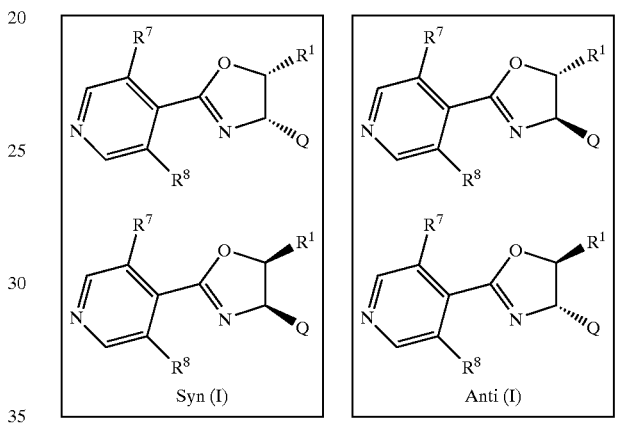

wherein $R^1$, Q, $R^7$ and $R^8$ are as defined in formula (I) provided that $R^1$ does not represent H.

In step a of Scheme C, the compound of formula (A) is reacted with an aminoalcohol (D) to afford a compound of formula (C). 1,2-Dichloroethane is the preferred solvent, however other polar aprotic solvents such as pyridine or THF can also be used.

The ring closure step b of Scheme C is similar to step d of Scheme A and provides the products of formula Syn (I) and Anti (I) which can be separated by using chromatographic techniques.

Alternatively, when Q represents

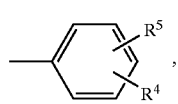

compounds of formula (I), in particular diastereomers Syn (Ib) and Anti (Ib), can be prepared by the method shown in Scheme D:

Scheme D

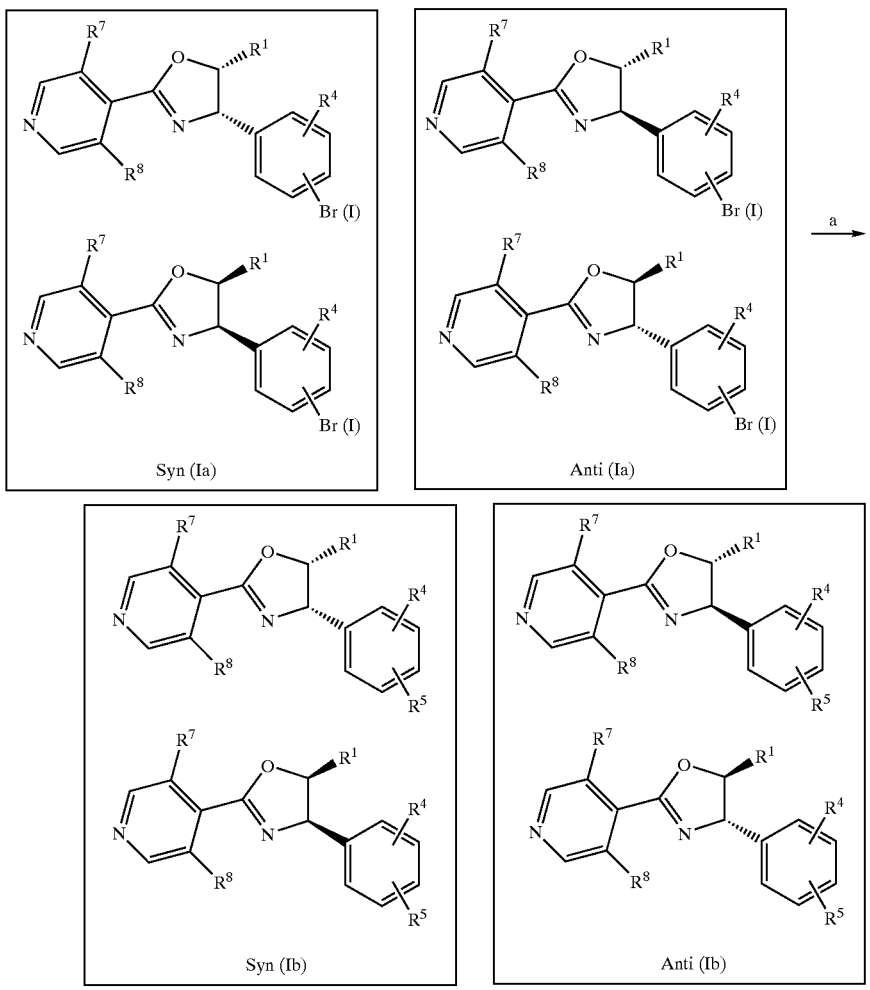

wherein $R^1$, Q, $R^4$, $R^5$, $R^7$ and $R^8$ are as defined in formula (I) provided that $R^1$ does not represent H.

The Suzuki coupling step a of Scheme D is similar to step a of Scheme B and provides products of formula Syn (Ib) and Anti (Ib) which can be separated by using chromatographic techniques.

Compounds of formula (D) can be prepared by the method illustrated in Scheme E:

Scheme E

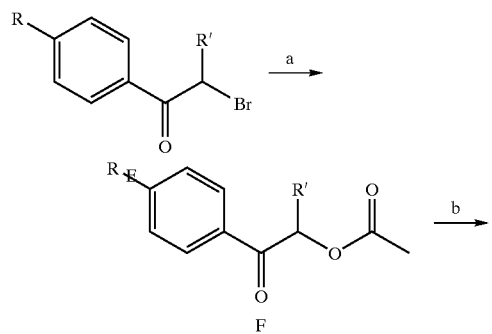

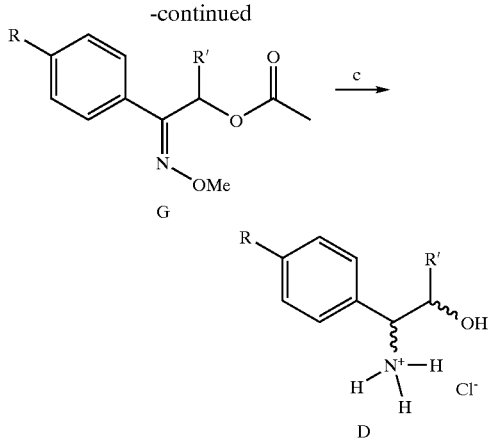

In step a of Scheme E, the compound of formula (E) is reacted with a mixture of potassium acetate and tetrabutylammonium chloride at refluxing temperature of dichloroethane to afford a compound of formula (F). Dichloroethane is the preferred solvent, however other chlorinated solvents such as dichloromethane or carbon tetrachloride can be used.

Alternatively the transformation can also be carried out using inorganic acetates such as sodium acetate with other phase transfer catalysts such as tetrabutylammonium bromide or iodide.

In step b of Scheme E, the compound of formula (F) is reacted with potassium acetate in ethanol followed by treatment with methoxylamine hydrochloride to provide the compound of formula (G).

In step c of Scheme E, the compound of formula (G) is reacted with a reducing agent such as sodium borohydride in trifluoroacetic acid to provide the compound of formula (D) in an organic solvent such as tetrahydrofuran. The reaction can be performed at ambient to refluxing temperature. The product can be isolated as a salt, preferably as the HCl salt.

EXAMPLES

Preparation of Starting Materials of Formula (D)

A) 4-[(1-Amino)-(2-hydroxy)ethyl]-iodobenzene (HCl salt)

2'-Bromo-4-Iodoacetophenone

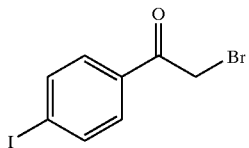

A 1 L round bottom flask, equipped with a mechanical stirrer, addition funnel, thermocouple and a reflux condenser attached to an alligator trap filled with aq. NaOH (2M), was charged with CuBr$_2$ (92.4 g, 0.414 mol) and ethyl acetate (320 mL). 4-Iodoacetophenone (53.4 g, 0.217 mol) was dissolved into chloroform (320 mL) and placed into the addition funnel. The chloroform solution was added to the ethyl acetate solution and the reaction mixture stirred at 70° C. for 6 hours then cooled to 25° C. for 16 hours. The CuBr salt was removed by filtering through Celite. The filtrate was washed with aq. saturated sodium bicarbonate (2×200 mL) and brine (100 mL). The organic layer was dried over sodium sulfate, filtered, and the solvents were removed under reduced pressure to give crude product contaminated with unreacted starting material. The product was purified by recrystallization from dichloromethane/hexane to give pure material as a tan solid (44.5 g, 63% yield): mp 109–111° C.

2'-Acetoxy-4-iodoacetophenone

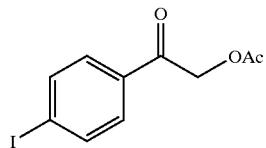

A 1 L round bottom flask equipped with a mechanical stirrer, thermocouple, and a reflux condenser was charged with 2'-bromo-4-iodoacetophenone (44.0 g, 0.135 mol), potassium acetate (19.9 g, 0.203 mol), benzyl triethylammonium chloride (1.5 g, 0.007 mol) and 1,2-dichloroethane (425 mL). The reaction mixture stirred at 70° C. for 4 hours then was cooled to 25° C. Water (250 mL) was added and the contents were shaken in a separatory funnel. The dichloroethane layer was separated and was washed with aq. saturated sodium bicarbonate (200 mL) and brine (100 mL). The dichloroethane was dried over sodium sulfate, filtered, and the solvents were removed under reduced pressure to give product as a tan solid (41.2 g, 97% yield): mp 103–107° C.

4-[(2-Acetoxy)-(1-methoxyimino)ethyl]-iodobenzene

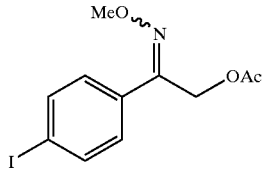

A 2 L round bottom flask equipped with a mechanical stirrer, thermocouple, and a reflux condenser was charged with 2'-acetoxy-4-iodoacetophenone (35.9 g, 0.118 mol), potassium acetate (13.9 g, 0.142 mol), methoxylamine hydrochloride (11.8 g, 0.142 mol) and ethyl alcohol (700 mL). The reaction mixture stirred at 70° C. for 8 hours then cooled to 25° C., and stirred at this temperature for 16 hours. The reaction mixture was filtered through Celite. The ethyl alcohol was removed under reduced pressure and the residue dissolved into ethyl acetate (500 mL). Water (100 mL) was added and the contents were shaken in a separator funnel. The ethyl acetate layer was separated and was washed with aq. saturated sodium bicarbonate (2×100 mL) and brine (100 mL). The ethyl acetate layer was dried over sodium sulfate, filtered, and the solvents were removed under reduced pressure to give product as an oil (37.4 g, 95% yield). Product is a 4:1 mixture of methoxime isomers.

4-[(1-Amino)-(2-hydroxy)ethyl]-iodobenzene (HCl salt)

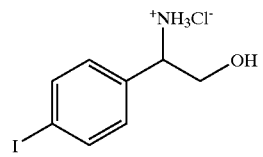

A 250 mL round bottom flask equipped with a magnetic stirrer, addition funnel, thermocouple, and a reflux condenser was charged with NaBH$_4$ (4.54 g, 0.120 mol) and THF (100 mL). Trifluoroacetic acid (13.7 g, 9.3 mL, 0.120 mol) was placed into the addition funnel and slowly added to the NaBH$_4$ suspension. A solution of 4-[(2-acetoxy)-(1-methoxyimino)ethyl]-iodobenzene (10.0 g, 0.030 mol) in 20 mL of THF was added to the addition funnel, and then slowly added to the trifluoroacetoxyborohydride suspension. The reaction mixture was heated to 70° C. for 3 hours and then cooled to 25° C. The pH was adjusted to <3 by the careful addition of conc. HCl to neutralize the remaining NaBH$_4$. The pH was adjusted to >9 with 50% aq. NaOH. Water (100 mL) and dichloromethane (200 mL) were added and the phases were separated. The aqueous phase was extracted with dichloromethane (3×100 mL). The combined organic phases were washed with brine, dried over sodium sulfate, filtered, and the solvents were removed under reduced pressure to give crude product. The product was purified by suspending in dichloromethane and bubbling anhydrous HCl gas to produce the HCl salt. The salt was filtered and dried to give product as a white solid (6.5 g, 72% yield): mp 200–206° C.

B) 2-Hydroxy-1-(4-iodophenyl)propanaminium chloride

1-Bromoethyl-(4-iodophenyl)ketone

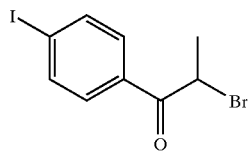

Finely powdered cuprous bromide (20.21 g, 91 mmol) was suspended in ethyl acetate (30 mL) and heated to reflux. A solution of ketone (14 g, 54 mmol) in chloroform (30 mL) was added dropwise over 10 minutes. After refluxing for 7 hours, the reaction was left to cool overnight and filtered through Celite. The filtrate was washed with saturated aqueous sodium bicarbonate (2×50 mL) and brine (50 mL), dried over magnesium sulfate and concentrated under reduced pressure. Recrystallization from hexane afforded a pale yellow solid. mp 76° C. Yield 12.2 g (66%). $^1$H NMR (CDCl$_3$) δ 7.83 (d, 2H), 7.72 (d, 2H), 5.21 (q, 2H), 1.87 (d, 3H). MI=338. IR (Liq film) cm$^{-1}$ 1677. Calculated for C$_9$H$_8$BrIO: C, 31.9%; H, 2.38%. Found: C, 32.2%; H, 2.5%.

1-Acetoxyethyl-(4-iodophenyl)ketone

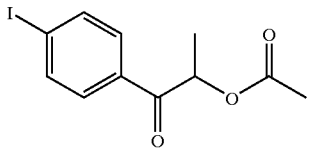

A suspension of the bromoketone (12 g, 35 mmol), potassium acetate (5.2 g, 53 mmol) and benzyl triethylammonium chloride (0.27 g, 1.2 mmol) in 1,2-dichloroethane (75 mL) was refluxed under nitrogen for 6 hours. After cooling to room temperature, water (35 mL) was added and the organic layer was collected. The organic layer was washed with saturated aqueous sodium bicarbonate (30 mL), and brine (20 mL), dried over magnesium sulfate and concentrated under reduced pressure to leave a yellow orange liquid. This was applied to a silica column and eluted with 5:1 hexane/ethyl acetate. Concentration of the major fraction gave 9.8 g (87%) of a pale yellow liquid. $^1$H NMR (CDCl$_3$) δ 7.84 (d, 2H), 7.64 (d, 2H), 5.87 (q, 2H), 2.14 (s, 3H), 1.56 (d, 3H). MI=318. IR (Liq film) cm$^{-1}$ 1740, 1699. Calculated for C$_{11}$H$_{11}$IO$_3$: C, 41.5%; H, 3.49%. Found: C, 41.04%; H, 3.60%.

2-Acetoxy-3-hydroxyamino-3-(4-iodophenyl)propane

To a solution of the acetate (4.5 g, 14 mmol) in absolute ethanol (80 mL) was added potassium acetate (1.66 g, 17 mmol) and methoxyamine hydrochloride (1.41 g, 17 mmol). The reactants were stirred under nitrogen at 63° C. for 10 hours and then refluxed for 3 hours. After cooling to room temperature and filtration through Celite, the filtrate was concentrated under reduced pressure. The residue was taken up in ethyl acetate (45 mL) and washed with water (15 mL), saturated aqueous bicarbonate (2×15 mL), and brine (20 mL) before drying over magnesium sulfate. Concentration under reduced pressure afforded 4.45 g (91%) of pale, yellow liquid. $^1$H NMR (CDCl$_3$) δ 7.75 & 7.69 (both d, 2H in total), 7.30 & 7.12 (d, 2H), 6.15 & 5.68 (q, 2H), 4.01 & 3.87 (s, 3H), 2.05 & 1.90 (s, 3H), 1.60 & 1.41 (d, 3H). MI=347. IR (Liq film) cm$^{-1}$ 1743.

2-Hydroxy-1-(4-iodophenyl)propanaminium chloride

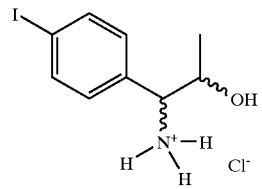

Sodium borohydride (0.44 g, 11.5 mmol) was suspended in dry tetrahydrofuran (10 mL) and cooled in an ice bath. Trifluoroacetic acid (1.31 g, 0.89 mL, 11.6 mmol) was then added dropwise over 10 minutes. The cooling bath was removed and a solution of the oxime (1 g, 2.9 mmol) in dry tetrahydrofuran (10 mL) was added over 10 minutes. The reaction was refluxed under nitrogen for 14 hours, cooled to room temperature and acidified to pH 3.0 using concentrated hydrochloric acid. After cooling in an ice bath, 50% aqueous sodium hydroxide was added to bring the pH to 11. A mixture of methylene chloride (20 mL) and water (20 mL) was then added to the reaction mixture. The organic layer was collected and the aqueous layer was re-extracted with methylene chloride (2×20 mL). The combined organic layers were washed with water (2×15 mL) and brine (15 mL) and dried over magnesium sulphate. Concentration under reduced pressure left a clear liquid that was taken up in methylene chloride (20 mL). Dry hydrogen chloride gas was bubbled through this solution for 15 minutes before stirring at room temperature for 30 minutes. White solids were collected by filtration. Yield 0.25 g (28%). $^1$H NMR (CDCl$_3$) δ 8.52 (br, 3H), 7.79 (m, 2H), 7.31 (m, 2H), 5.68 & 5.39 (d, total 1H), 4.18 & 3.96 (m, total 2H), 0.94 (s, 3H). MI=278.

C) 1-(4-Bromo-2-methylphenyl)-2-hydroxyethanaminium chloride

Ethyl (4-bromo-2-methylphenyl)(oxo)acetate

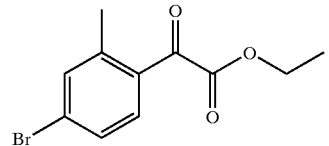

To a suspension of AlCl$_3$ (20.3 g, 152 mmol) in dichloroethane (250 mL, DCE) was added ethyl chlorooxoacetate (16.8 g, 123 mmol) at room temperature. To the resulting gold solution was added 3-bromotoluene (20.0 g, 117 mmol) and the dark solution was stirred at room temperature for 4 h. The reaction was cooled to 0° C. and saturated aqueous ammonium chloride was slowly added. The phases were separated and the DCE layer was washed with additional ammonium chloride, dried (Na$_2$SO$_4$), filtered, and the DCE removed in vacuo to give the crude product as a gold oil.

Flash chromatography (SiO$_2$; 0–3% Et$_2$O/Hexanes) gave ethyl (4-bromo-2-methylphenyl)-(oxo)acetate (16.2 g; 33%) as a gold oil. $^1$H NMR (CDCl$_3$) δ 1.41 (t, 3H, J=7.0 Hz), 2.58 (s, 3H), 4.43 (q, 2H, J=7.0 Hz), 7.44–7.48 (m, 2H), 7.58 (d, 1H, J=8.0 Hz); EI/MS 271 m/e (M$^+$).

Ethyl (4-bromo-2-methylphenyl)-(methoxyimino)ethanoate

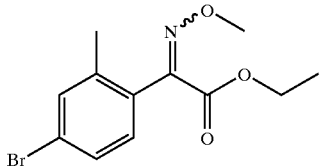

To a mixture of ethyl (4-bromo-2-methylphenyl)(oxo) acetate (10.0 g, 36.9 mmol) and KOAc (4.71 g, 48.0 mmol) in EtOH (185 mL) was added methoxylamine hydrochloride (4.00 g, 48.0 mmol) and the resulting milky suspension was stirred at 70° C. for 4 h. An additional 0.6 equivalents of KOAc and methoxylamine hydrochloride were added and the reaction mixture was stirred at 70° C. for 16 h. The reaction mixture was filtered through Celite, and the EtOH was removed under reduced pressure. The residue was dissolved into ethyl acetate (250 mL) and washed with aq. saturated sodium bicarbonate (2×100 mL) and brine (100 mL). The ethyl acetate layer was dried over Na$_2$SO$_4$ and filtered and the solvents were removed in vacuo to give the product as a colorless oil (11.0 g, 99%). Product is approximately a 1:1 mixture of methoxime isomers. $^1$H NMR (CDCl$_3$) δ 1.30–1.36 (m, 6H), 2.16 (s, 3H), 2.43 (s, 3 H), 4.01 (s, 3H), 4.04 (s, 3H), 4.30–4.38 (m, 4H), 6.98 (d, 1H, J=8.2 Hz), 7.22 (d, 1H, J=8.2 Hz), 7.33–7.40 (m, 4H).

1-(4-Bromo-2-methylphenyl)-2-hydroxyethanaminium chloride

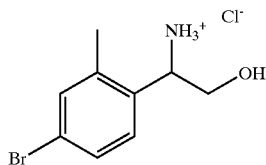

To a suspension of NaBH$_4$ (5.56 g, 147 mmol) in THF (100 mL) was added dropwise trifluoroacetic acid (16.7 g, 147 mmol) at a rate which maintained the reaction temperature between 25 and 35° C., and the resulting slurry was stirred at room temperature for 30 minutes. To the trifluoroacetoxyborohydride suspension was added a solution of ethyl (4-bromo-2-methylphenyl)-(methoxyimino)ethanoate (11.0 g, 36.7 mmol) in 20 mL of THF. The resulting light yellow mixture was stirred at reflux for 3.5 h and then at room temperature for 16 h. The excess NaBH$_4$ was neutralized by the careful addition of conc. HCl (pH<3). The pH was adjusted to >9 with 50% aq. NaOH and the alkaline mixture was diluted with water (100 mL). The THF was evaporated and the aq. residue was extracted with CH$_2$Cl$_2$ (3×100 mL). The organic extracts were washed with brine, dried (Na$_2$SO$_4$), filtered, and the CH$_2$Cl$_2$ was removed in vacuo to give crude product as a yellow oil. The oil was dissolved in CH$_2$Cl$_2$ and anhydrous HCl was bubbled into the solution. The resulting HCl salt was collected by vacuum filtration and dried to give the desired product as a white solid (5.7 g, 58%). mp 211–214° C. (d); $^1$H NMR (DMSO-d$_6$) δ 2.35 (s, 3H), 3.67 (d, 2H, J=6.0 Hz), 4.39 (m, 1H), ~5.30 (bs, 1H), 7.45–7.48 (m, 2H), 7.56 (d, 1H, J=8.8 Hz), 8.66 (s, 3H).

Example 1

Preparation of 2-(3,5-dichloro-4-pyridinyl)-4-(4-bromophenyl)oxazoline (Compound 4)

N-(4-bromophenylglycine methyl ester)-3,5-dichloro-4-pyridinyl carboxamide

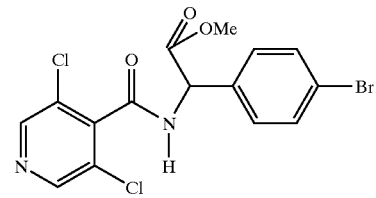

4-Bromophenylglycine methyl ester (36 mmol, 10.07 g) and 3,5-dichloro-4-pyridinyl carbonyl chloride (40 mmol, 8.40 g) were combined in 1,2-dichloroethane (200 mL) and pyridine (100 mmol, 8.09 mL) was added and the reaction stirred at ambient temperature for 18 hours. The reaction was washed with 1 M HCl and brine and dried over MgSO$_4$. Chromatography (SiO$_2$, EtOAc-Hex) afforded the product as a yellow oil (5.78 g).

N-1-(4-bromophenyl)-2-hydroxyethyl-(3,5-dichloro-4-pyridinyl)carboxamide

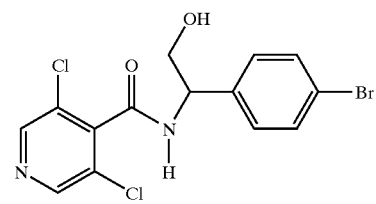

N-(4-Bromophenylglycine methyl ester)-3,5-dichloro-4-pyridinyl carboxamide (13.5 mmol, 5.65 g), sodium borohydride (54.0 mmol, 2.04 g), and calcium chloride (27.0 mmol, 3.0 g) were combined in THF (20 mL) and ethanol (40 mL) and stirred at ambient temperature for 36 hours. The yellow suspension was poured into 1 M Sodium Acetate (100 ml) and stirred 20–30 min. before extracting with EtOAc. The organic extract was washed with brine and dried over MgSO$_4$. Filtration and concentration in vacuo afforded a yellow solid (5.24 g). Chromatography (SiO2, EtOAc) afforded the product as a white solid. (2.44 g, 57.5% yield): mp 152–155° C.

2-(3,5-dichloro-4-pyridinyl)-4-(4-bromophenyl)oxazoline (Compound 4)

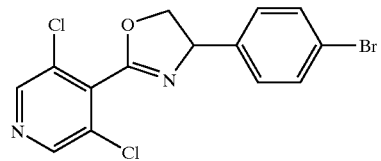

To a suspension of N-1-(4-bromophenyl)-2-hydroxyethyl-(3,5-dichloro-4-pyridinyl)carboxamide (5.84 mmol, 2.27 g) in 1,2-dichloroethane (80 mL) was added (diethylamino)sulfur trifluoride (DAST, 6.42 mmol, 0.85 mL) at −78° C. The reaction was allowed to warm slowly to room temperature and was stirred for 18 hours. The reaction upon completion was poured into ice containing NH$_4$OH (6 mL) and allowed to warm to ambient temperature before extracting into methylene chloride. The organic extract was washed with brine, dried over MgSO$_4$ and concentrated to an oil (2.60 g). Chromatography (SiO$_2$, 25% EtOAc-Hex) afforded the product as a white solid (1.63 g, 75% yield): mp 102–103° C.

Example 2

Preparation of 2-(3,5-dichloro-4-pyridinyl)-4-(4-iodophenyl)oxazoline (Compound 11)

N-1-(4-iodophenyl)-2-hydroxyethyl-(3,5-dichloro-4-pyridinyl)carboxamide

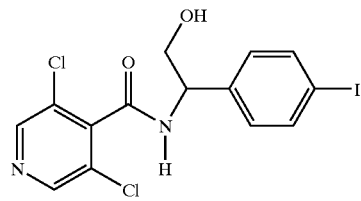

A 250 mL round bottom flask equipped with a stir bar, thermocouple, and a reflux condenser was charged with 4-[(1-amino)-(2-hydroxy)ethyl]-iodobenzene (HCl salt) (5.26 g, 17.6 mmol), triethylamine (4.3 g, 5.7 mL, 42.2 mmol) and THF (25 mL). The reaction mixture was cooled to 10° C. The 3,5-dichloro-4-pyridinyl carbonyl chloride (7.7 g, 17.6 mmol) was added to the THF solution keeping the temperature <30° C. The mixture was stirred at 25–30° C. for 2 hours. Dichloromethane (100 mL) and water (100 mL) were added and the phases were separated. The aqueous phase was extracted with dichloromethane (2×50 mL). The combined organic phases were washed with aq. 0.5 N HCl (50 mL) and brine (50 mL). The dichloromethane was dried over sodium sulfate, filtered, and the solvents removed under reduced pressure to give product as a tan solid (7.4 g, 96%): mp 177–180° C.

2-(3,5-dichloro-4-pyridinyl)-4-(4-iodophenyl)oxazoline (Compound 11)

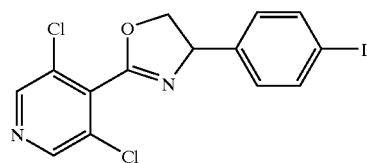

A 50 mL round bottom flask equipped with a stir bar, thermocouple, and a reflux condenser was charged with N-1-(4-iodophenyl)-2-hydroxyethyl-(3,5-dichloro-4-pyridinyl)carboxamide (1.07 g, 2.45 mmol) and dichloromethane (25 mL). The reaction mixture was cooled to −78° C. (Diethylamino)sulfur trifluoride (396 mg, 0.325 mL, 2.45 mmol) was added to the dichloromethane solution keeping the temperature <−70° C. Reaction was allowed to warm to 25° C. and was stirred overnight. The reaction mixture was poured into 50 g ice containing conc. ammonium hydroxide (5 mL). The phases were separated and the aqueous phase was extracted with dichloromethane (2×50 mL). The combined organic phases were washed with brine (50 mL), dried over sodium sulfate and filtered, and the solvents were removed under reduced pressure to give crude product as a tan solid. Chromatography gave pure 2-(3,5-dichloro-4-pyridinyl)-4-(4-iodophenyl)oxazoline as a tan solid (740 mg, 72%): mp 90–92° C.

Example 3

Preparation of 2-(3,5-dichloro-4-pyridinyl)-4-(4-(4-ethoxyphenyl)phenyl)oxazoline (Compound 12)

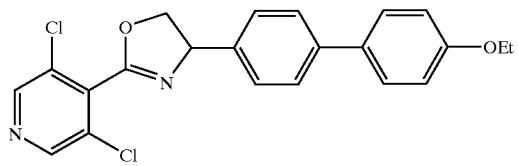

A solution of 2-(3,5-dichloro-4-pyridinyl)-4-(4-iodophenyl)oxazoline (0.2 g, 0.48 mmol), p-ethoxybenzeneboronic acid (0.095 g, 0.57 mmol), sodium carbonate (0.076 g, 0.72 mmol), dichlorobis(triphenylphosphine)palladium(II) (0.025 g) and tri-o-tolylphosphine (0.020 g) was heated at reflux for 12 h under an atmosphere of nitrogen. After cooling, 1N HCl (15 mL) was added and the mixture was extracted with diethyl ether (3×30 mL). The combined ether layers were dried over sodium sulfate, filtered and concentrated in vacuo. The residue was purified by chromatography (eluant, ether/hexane—1:1) to give the product as an off-white solid: mp 121–122° C.

The following compounds were prepared according to the procedure of Example 3.

Compound 5

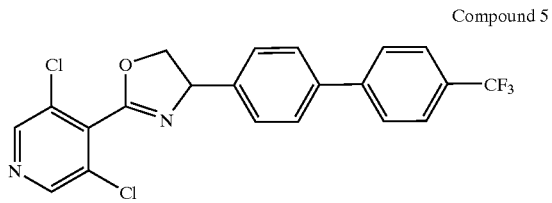

Isolated as a white solid (62% yield): mp 144–146° C.; $^1$H NMR (300 MHz, CDCl$_3$) δ 8.64 (s, 2H), 7.72 (s, 4H), 7.68–7.64 (Ar-m, 2H), 7.54–7.51 (Ar-m, 2H), 5.62 (dd, 1H, J=8.6, 10.2 Hz), 4.97 (dd, 1H, J=8.5, 10.4 Hz), 4.43(dd, 1H, J=8.5, 8.5 Hz); EI/MS 437 m/e (M$^+$); Anal. Calcd. for C$_{21}$H$_{13}$Cl$_2$F$_3$N$_2$O$_1$: C, 57.69; H, 3.00; N, 6.41. Found: C, 57.64; H, 3.02; N, 6.33.

Compound 6

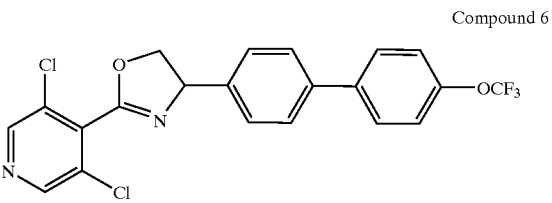

Isolated as a white solid (20% yield): mp 113–115° C.; $^1$H NMR (300 MHz, CDCl$_3$) δ 8.61 (s, 2H), 7.61–7.58 (Ar-m, 4H), 7.48 (d, 2H, J=8.4 Hz), 7.29 (d, 2H, J=7.7 Hz), 5.58 (dd, 1H, J=8.8, 10.2 Hz), 4.94 (dd, 1H, J=8.6, 10.2 Hz), 4.41 (dd, 1H, J=8.6, 8.6 Hz); EI/MS 352 m/e (M$^+$); Anal. Calcd. for C$_{21}$H$_{13}$Cl$_2$F$_3$N$_2$O$_2$: C, 55.65; H, 2.89; N, 6.18. Found: C, 55.24; H, 2.82; N, 6.09.

Compound 7

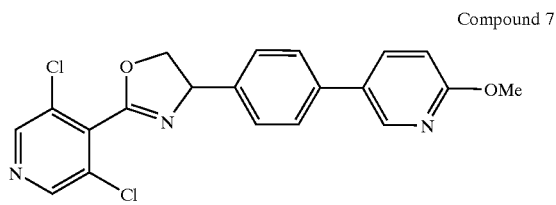

Isolated as a white solid (34% yield): mp 145–147° C.; $^1$H NMR (300 MHz, CDCl$_3$) δ 8.61 (s, 2H), 8.39 (d, 1H, J=2.6 Hz), 7.58–7.55 (d, 2H, J=8.4 Hz), 7.47 (d, 2H, J=8.4 Hz), 6.82 (d, 1H, J=8.8 Hz), 5.58 (dd, 1H, J=8.6, 10.2 Hz), 4.94 (dd, 1H, J=8.4, 10.2 Hz), 4.40 (dd, 1H, J=8.6, 8.6 Hz), 3.98 (s, 3H); EI/MS 400 m/e (M$^+$).

Compound 8

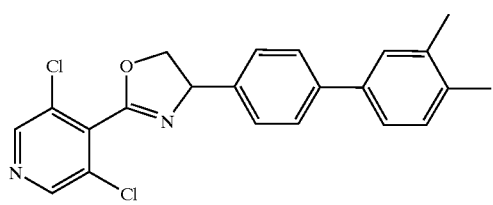

Isolated as a tan solid (63% yield): mp 112–115° C.; $^1$H NMR (300 MHz, CDCl$_3$) δ 8.60 (s, 2H), 7.61 (d, J=8.4 Hz, 2H), 7.44 (d, J=8.4 Hz, 2H), 7.37–7.32 (m, 2H), 7.20 (d, J=8.1 Hz, 1H), 5.56 (dd, J=8.8, 10.2 Hz, 1H), 4.92 (dd, J=8.8, 10.4 Hz, 1H), 4.41 (dd, J=8.8, 8.8 Hz, 1H), 2.33 (s, 3H), 2.31 (s, 3H); EI/MS 397 m/e (M$^+$).

Compound 9

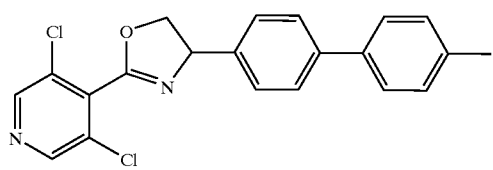

Isolated as a tan solid (2% yield): mp 107–120° C.; $^1$H NMR (300 MHz, CDCl$_3$) δ 8.61 (s, 2H), 7.63 (d, J=2.2 Hz, 2H), 7.62–7.44 (m, 4H), 7.26 (d, J=7.6 Hz, 2H), 5.57 (dd, J=8.7, 10.2 Hz, 1H), 4.93 (dd, J=8.4, 10.2 Hz, 1H), 4.41 (dd, J=8.7, 8.4 Hz, 1H), 2.40 (s, 3H); EI/MS 382 m/e (M$^+$).

Compound 10

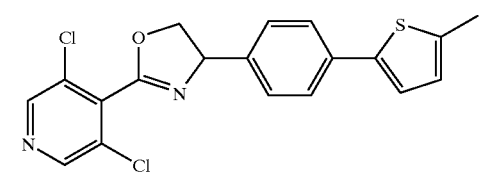

Isolated as a white solid (19% yield): mp 128–136° C.; $^1$H NMR (300 MHz, CDCl$_3$) δ 8.61 (s, 2H), 7.57 (d, J=8.4 Hz, 2H), 7.37 (d, J=8.4 Hz, 2H), 7.12 (d, J=3.6 Hz, 1H), 6.74 (dd, J=1.0, 3.6 Hz, 1H), 5.53 (dd, J=8.7, 10.2 Hz, 1H), 4.91 (dd, J=8.4, 10.2 Hz, 1H), 4.37 (dd, J=8.4, 8.4 Hz, 1H), 2.51 (s, 3H); EI/MS 388 m/e (M$^+$).

Compound 13

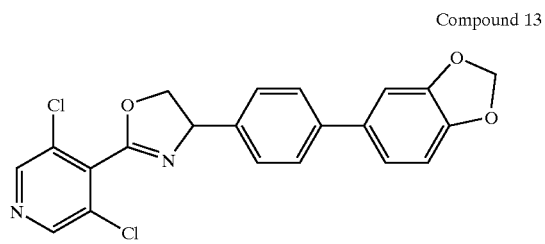

33% yield, mp 109–110° C.; $^1$H NMR (CDCl$_3$) δ 4.33 (t, 1H, J=2.8 Hz), 4.84 (dd, 1H, J=2.8 Hz), 5.48 (dd, 1H, J=3.5 Hz), 5.92 (s, 2H), 6.80 (d, 2H, J=2.2 Hz), 6.98 (d, 2H, J=2.2 Hz), 7.35 (d, 2H, J=2.2 Hz), 7.45 (d, 2H, J=2.2 Hz), 8.53 (s, 2H); MS m/e 412 (M$^+$).

Compound 14

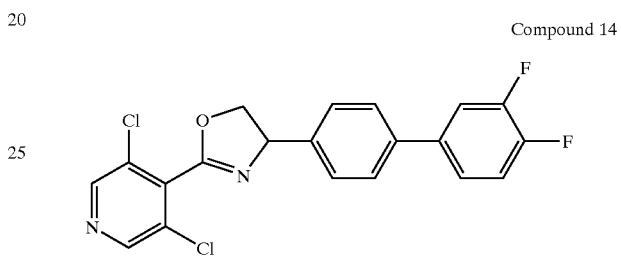

Isolated as a yellow solid (53% yield): mp 130° C.; $^1$H NMR (300 MHz, CDCl$_3$) δ 8.61 (s, 2H), 7.55 (d, 2H), 7.48 (d, 2H), 7.42–7.17 (m, 3H), 5.58 (dd, 1H), 4.94 (dd, 1H), 4.39 (dd, 1H); EI/MS 404 m/e (M$^+$).

Compound 15

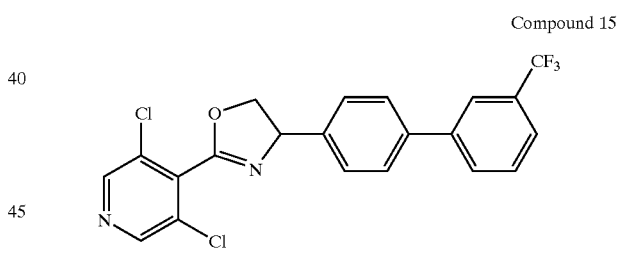

15% yield as a clear oil: $^1$H NMR (300 MHz, CDCl$_3$) δ 8.62 (s, 2H), 7.84–7.49 (m, 8H), 5.60 (dd, 1H), 4.95 (dd, 1H), 4.41 (dd, 1H); EI/MS 437 m/e (M$^+$).

Compound 16

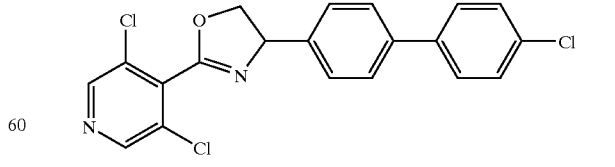

20% yield as an orange solid: mp 153–157° C.; $^1$H NMR (300 MHz, CDCl$_3$) δ 8.61 (s, 2H), 7.60–7.39 (m, 8H), 5.58 (dd, 1H), 4.94 (dd, 1H), 4.40 (dd, 1H); EI/MS 404 m/e (M$^+$).

Compound 17

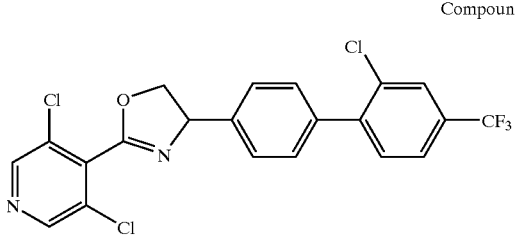

Isolated as a brown gum (74% yield): ¹H NMR (300 MHz, CDCl₃) δ 8.62 (s, 2H), 7.75 (s, 1H), 7.57 (d, 1H), 7.49 (br, 5H), 5.60 (dd, 1H), 4.95 (dd, 1H), 4.45 (dd, 1H); EI/MS 470 m/e (M⁺).

Compound 18

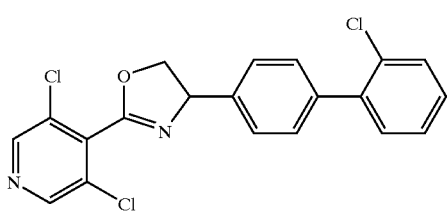

Isolated as a dark amber oil (20% yield): ¹H NMR (300 MHz, CDCl₃) δ 8.61 (s, 2H), 7.49–7.28 (m, 8H), 5.59 (dd, 1H), 4.95 (dd, 1H), 4.45 (dd, 1H); EI/MS 404 m/e (M⁺).

Compound 19

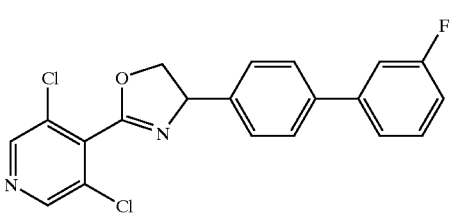

Isolated as an orange solid (80% yield): mp 98–103° C.; ¹H NMR (300 MHz, CDCl₃) δ 8.61 (s, 2H), 7.61 (d, J=8.42 Hz, 2H), 7.48 (d, J=8.06 Hz, 2H), 7.42–7.36 (m, 2H), 7.31–7.27 (m, 1H), 7.07–7.02 (m, 1H), 5.58 (dd, J=9.52, 9.89 Hz, 1H), 4.94 (dd, J=10.25, 8.42 Hz, 1H), 4.41 (dd, J=8.42, 8.42 Hz, 1H); EI/MS 387 m/e (M⁺).

Compound 20

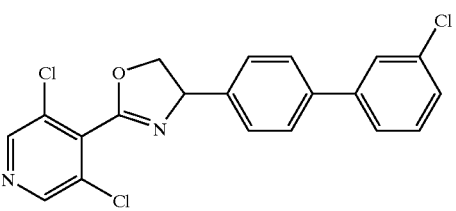

Isolated as an amber oil (63% yield): ¹H NMR (300 MHz, CDCl₃) δ 8.61 (s, 2H), 7.62–7.33 (m, 8H), 5.58 (dd, 1H), 4.94 (dd, 1H), 4.40 (dd, 1H); EI/MS 404 m/e (M⁺).

Compound 21

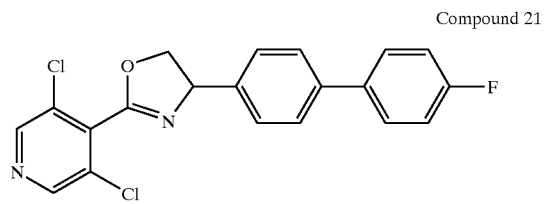

Isolated as a light brown solid (27% yield): mp 146–149° C.; ¹H NMR (300 MHz, CDCl₃) δ 8.61 (s, 2H), 7.59–7.52 (m, 4H), 7.46 (d, J=8.42 Hz, 2H), 7.16–7.10 (m, 2H), 5.57 (dd, J=10.25, 8.79 Hz, 1H), 4.93 (dd, J=10.44, 8.79 Hz, 1H), 4.40 (dd, J=8.61, 8.79 Hz, 1H); EI/MS 386 m/e (M⁺).

Compound 22

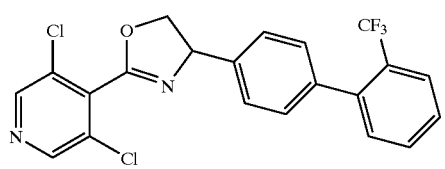

Isolated as a light tan solid (80% yield): mp 97–98° C.; ¹H NMR (300 MHz, CDCl₃) δ 8.61 (s, 2H), 7.75 (d, J=7.69 Hz, 1H), 7.56 (t, J=7.42 Hz, 1H), 7.49–7.42 (m, 4H), 7.37–7.30 (m, 2H), 5.58 (dd, J=9.61, 10.16 Hz, 1H), 4.95 (dd, J=10.16, 8.52 Hz, 1H), 4.45 (dd, J=8.79, 8.79 Hz, 1H), EI/MS 436 m/e (M⁺).

Compound 23

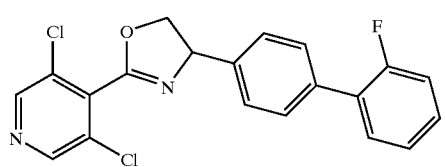

Isolated as a light orange solid (92% yield): mp 91–93° C.; ¹H NMR (300 MHz, CDCl₃) δ 8.61 (s, 2H), 7.61–7.58 (m, 2H), 7.49–7.41 (m, 2H), 7.36–7.29 (m, 2H), 7.24–7.12 (m 2H), 5.59 (dd, J=10.25, 8.79 Hz, 11H), 4.94 (dd, J=10.25, 8.42 Hz, 1H), 4.42 (dd, J=8.61, 8.42 Hz, 1H); EI/MS 386 m/e (M⁺).

Compound 24

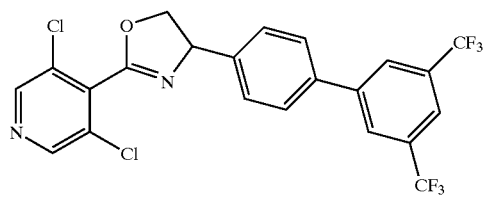

Isolated as an orange foam (93% yield): ¹H NMR (300 MHz, CDCl₃) δ 8.62 (s, 2H), 8.02 (broad m, 4H), 7.86 (broad m, 1H), 7.68–7.64 (m, 2H), 7.56–7.53 (m, 2H), 5.62 (dd, J=10.25, 8.79 Hz, 1H); 4.96 (dd, J=10.44, 8.79 Hz, 1H), 4.40 (dd, J=8.62, 8.79 Hz, 1H); EI/MS 504 m/e (M⁺).

Compound 25

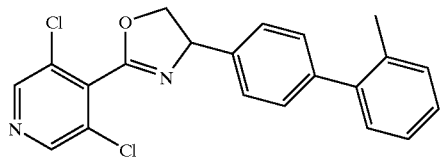

Isolated as an off-white solid (34% yield): mp 78–81° C.; ¹H NMR (300 MHz, CDCl₃) δ 8.61 (s, 2H), 7.44 (d, J=8.0 Hz, 2H), 7.37 (d, J=8.0 Hz, 2H), 7.28–7.21 (m, 4H), 5.58 (dd, J=9.1, 10.2 Hz, 1H), 4.95 (dd, J=8.6, 10.4 Hz, 1H), 4.45 (t, J=8.6 Hz, 1H), 2.28 (s, 3H); EI/MS 382 m/e (M⁺); Anal. Calcd. for $C_{21}H_{16}Cl_2N_2O$: C, 65.81; H, 4.21; N, 7.31. Found: C, 65.67; H, 4.26; N, 7.36.

Compound 26

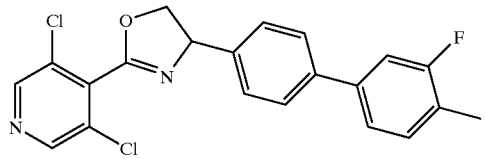

Isolated as a brown solid (30% yield): mp 88–91° C.; ¹H NMR (300 MHz, CDCl₃) δ 8.61 (s, 2H), 7.59 (d, 2H), 7.46 (d, 2H), 7.29–7.22 (m, 3H), 5.57 (dd, 1H), 4.93 (dd, 1H), 4.40 (dd, 1H), 2.31 (d, 3H); EI/MS 400 m/e (M⁺).

Compound 27

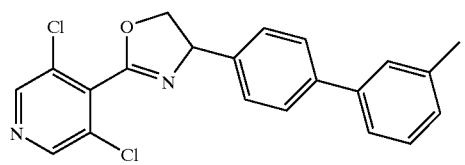

Isolated as an off-white solid (33% yield): mp 84–87° C.; ¹H NMR (300 MHz, CDCl₃) δ 8.61 (s, 2H), 7.62 (d, J=8.4 Hz, 2H), 7.46 (d, J=8.0 Hz, 2H), 7.41–7.31 (m, 3H), 7.17 (d, J=7.3 Hz, 1H), 5.58 (dd, J=8.7, 10.2 Hz, 1H), 4.94 (dd, J=8.4, 10.2 Hz, 1H), 4.42 (dd, J=8.4, 8.7 Hz, 1H), 2.43 (s, 3H); EI/MS 382 m/e (M⁺).

Compound 28

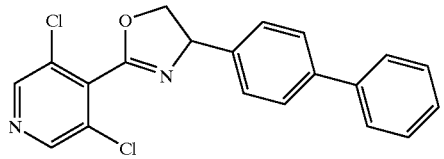

Isolated as a brown solid (53% yield): mp 141–143° C.; ¹H NMR (300 MHz, CDCl₃) δ 8.61 (s, 2H), 7.62 (dd, J=7.3, 9.5 Hz, 4H), 7.49–7.36 (m, 5H), 5.59 (dd, J=8.7, 10.2 Hz, 1H), 4.94 (dd, J=8.4, 10.2 Hz, 1H), 4.42 (dd, J=8.4, 8.7 Hz, 1H); EI/MS 368 m/e (M⁺).

Compound 29

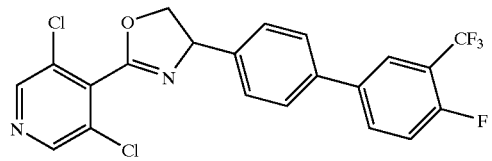

Isolated as a yellow oil (48% yield): ¹H NMR (300 MHz, CDCl₃) δ 8.61 (s, 2H), 7.63–7.49 (m, 6H), 7.32 (m, 1H), 5.60 (dd, J=8.8, 10.4 Hz, 1H), 4.95 (dd, J=8.8, 10.4 Hz, 1H), 4.42 (dd, J=8.8, 8.8 Hz, 1H); EI/MS 455 m/e (M⁺).

Compound 30

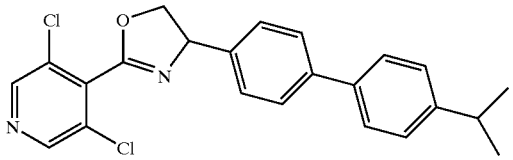

Isolated as a light yellow solid (21% yield): mp 123–128° C.; ¹H NMR (300 MHz, CDCl₃) δ 8.61 (s, 2H), 7.61 (d, J=8.0 Hz, 2H), 7.53 (d, J=8.0 Hz, 2H), 7.46 (d, J=8.4 Hz, 2H), 7.31 (d, J=8.4 Hz, 2H), 5.57 (dd, J=8.7, 10.2 Hz, 1H), 4.93 (dd, J=8.4, 10.2 Hz, 1H), 4.40 (dd, J=8.4, 8.7 Hz, 1H), 2.96 (h, J=6.9 Hz, 1H), 1.29 (d, J=6.9 Hz, 6H); EI/MS 410 m/e (M⁺).

Compound 31

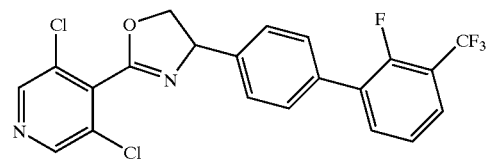

Isolated as a white solid (71% yield): mp 98–99° C.; ¹H NMR (300 MHz, CDCl₃) δ 8.61 (s, 2H), 7.66–7.57 (m, 4H), 7.51 (d, 2H), 7.31 (t, 1H), 5.60 (dd, 1H), 4.96 (dd, 1H), 4.42 (dd, 1H); EI/MS 454 m/e (M⁺).

Compound 32

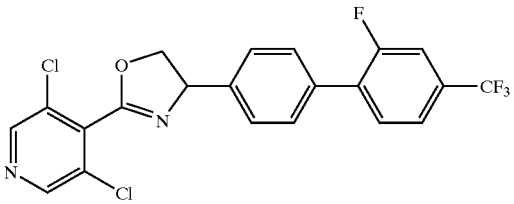

26% yield as a yellow oil: ¹H NMR (300 MHz, CDCl₃) δ 8.61 (s, 2H), 7.61–7.13 (m, 7H), 5.60 (dd, 1H), 4.96 (dd, 1H), 4.42 (dd, 1H); EI/MS 455 m/e (M⁺).

Compound 33

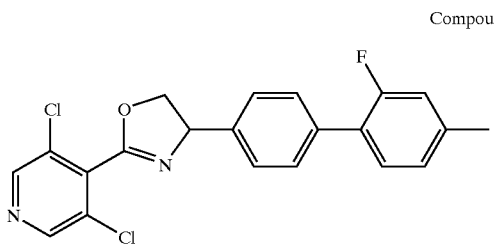

67% yield as a yellow oil: $^1$H NMR (300 MHz, CDCl$_3$) δ 8.60 (s, 2H), 7.56 (d, 2H), 7.45 (d, 2H), 7.34–6.99 (m, 3H), 5.58 (dd, 1H), 4.94 (dd, 1H), 4.41 (dd, 1H), 2.39 (s, 3H); EI/MS 400 m/e (M$^+$).

Compound 34

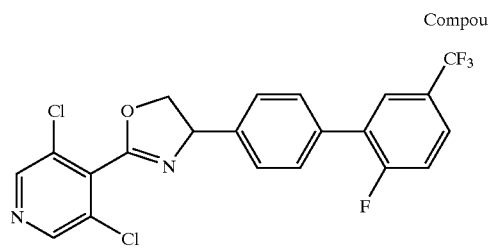

Isolated as a yellow oil (85% yield): $^1$H NMR (300 MHz, CDCl$_3$) δ 8.58 (s, 2H), 7.68 (d, 1H), 7.55 (m, 3H), 7.48 (d, 2H), 7.22 (m, 1H), 5.55 (dd, 1H), 4.90 (dd, 1H), 4.38 (dd, 1H); EI/MS 455 m/e (M$^+$).

Compound 35

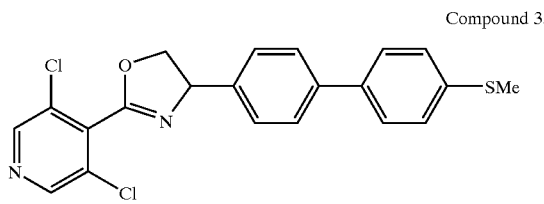

Isolated as a tan solid (83% yield): mp 170–173° C.; $^1$H NMR (300 MHz, CDCl$_3$) δ 8.61 (s, 2H), 7.61 (d, J=8.4 Hz, 2H), 7.53 (d, J=8.4 Hz, 2H), 7.46 (d, J=8.4 Hz, 2H), 7.33 (d, J=8.4 Hz, 2H), 5.51 (dd, J=8.4, 10.3 Hz, 1H), 4.93 (dd, J=8.4, 10.3 Hz, 1H), 4.41 (dd, J=8.4, 8.4 Hz, 1H), 2.53 (s, 3H); EI/MS 415 m/e (M$^+$).

Compound 36

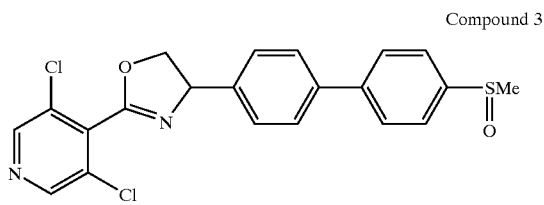

Isolated as a yellow solid (68% yield): mp 153–156° C.; $^1$H NMR (300 MHz, CDCl$_3$) δ 8.61 (s, 2H), 7.73 (m, 4H), 7.65 (d, J=8.4 Hz, 2H), 7.50 (d, J=8.4 Hz, 2H), 5.60 (dd, J=8.8, 10.1 Hz, 1H), 4.95 (dd, J=8.8, 10.1 Hz, 1H), 4.41 (dd, J=8.8, 8.8 Hz, 1H), 2.77 (s, 3H); EI/MS 431 m/e (M$^+$).

Compound 37

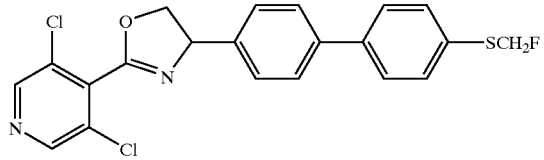

Isolated as a tan solid (76% yield): mp 135–138° C.; $^1$H NMR (300 MHz, CDCl$_3$) δ 8.61 (s, 2H), 7.61 (d, J=8.1 Hz, 2H), 7.57 (s, 4H), 7.48 (d, J=8.4 Hz, 2H), 5.76 (d, J$_{H-F}$=52.7 Hz, 2H), 5.58 (dd, J=8.4, 10.3 Hz, 1H), 4.94 (dd, J=8.4, 10.3 Hz, 1H), 4.41 (dd, J=8.4, 8.4 Hz, 1H); EI/MS 433 m/e (M$^+$).

Example 4

Preparation of 2-(3,5-difluoro-4-pyridinyl)-4-(4-iodophenyl)oxazoline (Compound 38)

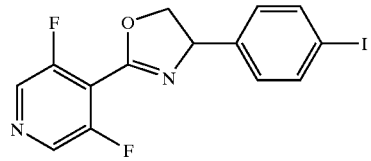

The procedure of Example 2 was repeated using 3,5-difluoro-4-pyridinyl carbonyl chloride as the starting material. Product was isolated as an off-white solid (1.52 g, 62%): mp 84–86° C.; $^1$H NMR (CDCl$_3$) δ 8.49 (s, 2H), 7.72 (d, 2H, J=8.4 Hz), 7.06 (d, 2H, J=8.4 Hz), 5.45 (dd, 1H, J=10.3, 8.8 Hz), 4.85 (dd, 1H, J=10.3, 8.4 Hz), 4.29 (dd, 1H, J=8.8, 8.4 Hz); EI/MS 386 m/e (M$^+$); For C$_{14}$H$_9$F$_2$N$_2$O; Calculated: C, 43.55; H, 2.35; N, 7.25; Found: C, 43.46; H, 2.40; N, 7.17.

Example 5

Preparation of 2-(3,5-difluoro-4-pyridinyl)-4-(4-(4-trifluoromethylphenyl)phenyl)-oxazoline (Compound 39)

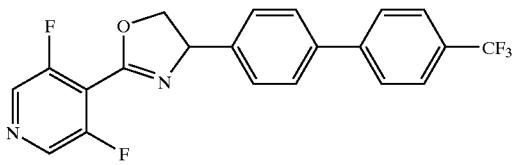

The procedure of Example 3 was repeated using the appropriate starting materials and the product was isolated as a tan solid (73% yield): mp 136–138° C.; $^1$H NMR (300 MHz, CDCl$_3$) δ 8.50 (s, 2H), 7.69 (s, 4H), 7.62 (d, J=8.4 Hz, 2H), 7.43 (d, J=8.4 Hz, 2H), 5.56 (dd, J=8.4, 10.1 Hz, 1H), 4.92 (dd, J=8.4, 10.1 Hz, 1H), 4.39 (dd, J=8.4, 8.4 Hz, 1H); EI/MS 404 m/e (M$^+$).

The following compound was similarly prepared according to the procedure of Example 3.

Compound 40

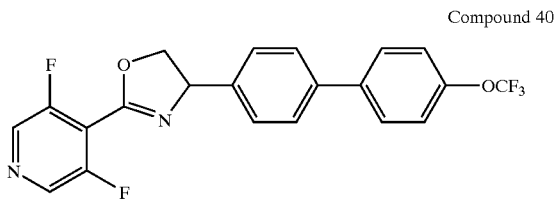

Isolated as an orange solid (55% yield): mp 92–95° C.; $^1$H NMR (300 MHz, CDCl$_3$) δ 8.50 (s, 2H), 7.60–7.57 (m, 4H), 7.40 (d, J=8.1 Hz, 2H), 7.28 (d, J=8.1 Hz, 2H), 5.55 (dd, J=8.4, 10.2 Hz, 1H), 4.89 (dd, J=8.4, 10.2 Hz, 1H), 4.38 (dd, J=8.4, 8.4 Hz, 1H); EI/MS 420 m/e (M$^+$).

Example 6

Preparation of 4-[4-(4-bromo-2-methylphenyl)4,5-dihydro-1,3-oxazol-2-yl]-3,5-dichloropyridine (Compound 41)
N-[1-(4-bromo-2-methylphenyl)-2-hydroxyethyl]-3,5-dichloroisonicotinamide

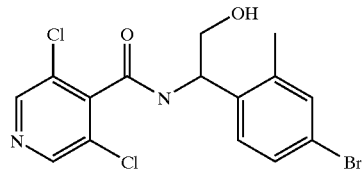

To a suspension of 1-(4-bromo-2-methylphenyl)-2-hydroxyethanaminium chloride (3.0 g, 11.2 mmol) in THF (100 mL) was added dropwise triethylamine (2.85 g, 28.1 mmol) at 0° C. To the resulting white slurry was added dropwise a solution of 3,5-dichloroisonicotinoyl chloride, freshly prepared from lithium 3,5-dichloroisonicotinate (2.34 g, 11.8 mmol), and the resulting tan slurry was warmed to room temperature and stirred for 16 h. The reaction was diluted with water and the THF was removed in vacuo. The aqueous residue was extracted with CH$_2$Cl$_2$ (2×100 mL), and the organic extracts were combined, washed with 2 N HCl, washed with brine, dried (Na$_2$SO$_4$), filtered, and the CH$_2$Cl$_2$ removed in vacuo to give the crude product as an oily, brown solid. Trituration with Et$_2$O afforded the desired product (3.0 g, 67%) as a tan solid: mp 192–194° C.; $^1$H NMR (DMSO-d$_6$) δ 2.45 (s, 3H), 3.88–3.97 (m, 2H), 5.40–5.46 (m, 1H), 6.66 (d, 1H, J=7.0 Hz), 7.21–7.39 (m, 3H), 8.50 (s, 2H); EI/MS 404 m/e (M$^+$).
4-[4-(4-bromo-2-methylphenyl)-4,5-dihydro-1,3-oxazol-2-yl]-3,5-dichloropyridine (Compound 41)

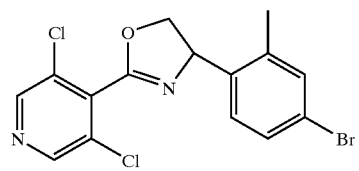

To a suspension of N-[1-(4-bromo-2-methylphenyl)-2-hydroxyethyl]-3,5-dichloroisonicotinamide (2.90 g, 7.2 mmol) in CH$_2$Cl$_2$ (75 mL) was added dropwise (diethylamino)sulfur trifluoride (1.16 g, 7.2 mmol) at −78° C. The cooling bath was removed and the light orange mixture was warmed to room temperature. The resulting light orange solution was stirred at room temperature for 16 h. The reaction mixture was poured into 100 g of ice containing conc. NH$_4$OH (25 mL). The phases were separated and the aqueous phase was extracted with CH$_2$Cl$_2$ (2×50 mL). The organic extracts were combined, washed with brine, dried (Na$_2$SO$_4$), filtered, and the solvents removed in vacuo to give crude product as a tan solid. Flash chromatography (SiO$_2$; 20% EtOAc/hexanes) afforded pure product as a white solid (2.25 g, 81%): mp 93–95° C.; $^1$H NMR (CDCl$_3$) δ 2.32 (s, 3H), 4.17 (dd, 1H, J=8.7, 8.7 Hz), 4.94 (dd, 1H, J=8.4, 10.4 Hz), 5.65 (dd, 1H, J=9.7, 9.7 Hz), 7.32–7.39 (m, 3H), 8.60 (s, 2H); EI/MS 386 m/e (M$^+$); Anal. Calcd. for C$_{15}$H$_{11}$BrCl$_2$N$_2$O: C, 46.67; H, 2.87; N, 7.26. Found: C, 46.85; H, 2.77; N, 7.19.

Example 7

Preparation of 2-(3,5-dichloro-4-pyridinyl)-4-(4-(4-trifluoromethylphenyl)-2-methylphenyl)-oxazoline (Compound 43)

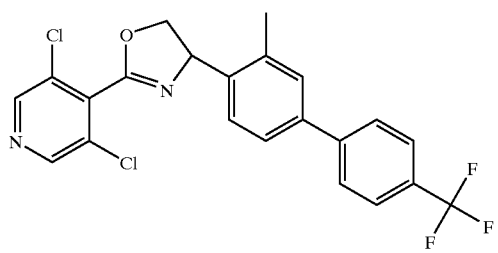

To a solution of 4-[4-(4-bromo-2-methylphenyl)-4,5-dihydro-1,3-oxazol-2-yl]-3,5-dichloropyridine (0.5 g, 1.3 mmol) in EtOH (13 mL) was added K$_2$CO$_3$ (0.27 g, 2.0 mmol) and 4-(trifluoromethyl)benzeneboronic acid (0.25 g, 1.3 mmol). The mixture was degassed prior to the addition of (PPh$_3$)$_4$Pd(0) (3–10 mol %), and then stirred at reflux for 16 h. Additional boronic acid was added and the mixture was stirred at reflux for 3 h. The reaction was cooled to room temperature and stirred for 48 h. The reaction was diluted with CH$_2$Cl$_2$ (100 mL), washed with 2 N HCl, and the aqueous was extracted with additional CH$_2$Cl$_2$. The organic extracts were combined, washed with brine, dried (Na$_2$SO$_4$) and filtered, and the solvent was removed in vacuo to give the crude product as a light yellow oil. Flash chromatography (SiO$_2$; 0–20% Et$_2$O/hexanes) afforded a colorless oil. The oil was dissolved in hot hexane and then cooled in the freezer. Vacuum filtration afforded the product (0.2 g, 34%) as a white crystalline solid: mp 129–131° C.; $^1$H NMR (CDCl$_3$) δ 2.46 (s, 3H), 4.28 (dd, 1H, J=8.2, 9.0 Hz), 5.01 (dd, 1H, J=8.2, 10.4 Hz), 5.78 (dd, 1H, J=9.0, 10.4 Hz), 7.45 (d, 1H, J=1.8 Hz), 7.51 (dd, 1H, J=1.8, 8.0 Hz), 7.59 (d, 1H, J=8.0 Hz), 7.70 (s, 4H), 8.63 (s, 2H); Anal. Calcd. for C$_{22}$H$_{15}$Cl$_2$F$_3$N$_2$O: C, 58.55; H, 3.35; N, 6.21. Found: C, 58.54; H, 3.35; N, 6.17.

The following compound was similarly prepared according to the procedure of Example 7.

Compound 42

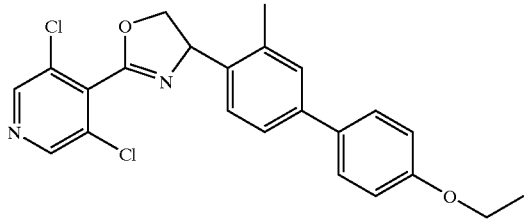

Isolated as a white solid (43% yield): mp 127–129° C.; $^1$H NMR (CDCl$_3$) δ 1.45 (t, 3H, J=7.0 Hz), 2.43 (s, 3H), 4.08 (q, 2H, J=7.0 Hz), 4.28 (dd, 1H, J=8.6, 8.6 Hz), 4.98 (dd, 1H, J=8.2, 10.4 Hz), 5.65 (dd, 1H, J=9.2, 10.2 Hz), 6.96 (d, 2H, J=8.8 Hz), 7.40–7.47 (m, 3H), 7.51 (d, 2H, J=8.8 Hz), 8.62 (s, 2H); EI/MS 427 m/e (M$^+$); Anal. Calcd. for C$_{23}$H$_{20}$Cl$_2$N$_2$O: C, 64.65; H, 4.72; N, 6.65. Found: C, 64.31; H, 4.76; N, 6.49.

Example 8

Preparation of 2-(3,5-dichloro-4-pyridinyl)-4-(4-(4-trifluoromethoxyphenyl)-2-methylphenyl)-oxazoline (Compound 44)

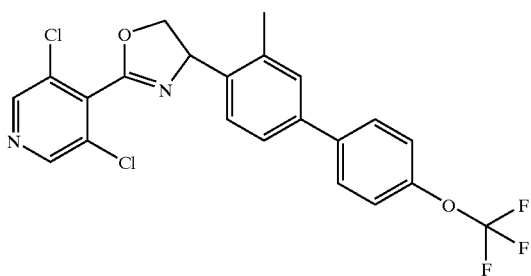

To a mixture of 4-[4-(4-bromo-2-methylphenyl)-4,5-dihydro-1,3-oxazol-2-yl]-3,5-dichloropyridine (0.46 g, 1.2 mmol), 4-(trifluoromethoxy)benzeneboronic acid (0.26 g, 1.2 mmol), NA$_2$CO$_3$ (0.18 g, 1.7 mmol), and tri-o-tolylphosphine (0.07 g, 0.2 mmol) in 10% H$_2$O/CH$_3$CN (13.2 mL) was added (PPh$_3$)$_2$PdCl$_2$ (0.08 g, 0.1 mmol) and the resulting amber mixture was stirred at reflux for 16 h. The black mixture was cooled to room temperature, diluted with 2N HCl, and the acetonitrile was removed in vacuo. The aqueous residue was extracted with CH$_2$Cl$_2$(2×150 mL), and the organic extracts were combined, washed with brine, dried (Na$_2$SO$_4$) and filtered, and the solvent was removed in vacuo to give the crude product as an orange oil. Flash chromatography (SiO$_2$; 0–30% Et$_2$O/hexanes) afforded a colorless oil. The oil was dissolved in hot hexane and then cooled in the freezer. Vacuum filtration afforded the target compound (0.16 g, 28%) as a white solid: mp 100–102° C.; $^1$H NMR (CDCl$_3$) δ 2.44 (s, 3H), 4.27 (dd, 1H, J=8.6, 8.6 Hz), 5.00 (dd, 1H, J=8.2, 10.4 Hz), 5.77 (dd, 1H, J=10.2, 9.2 Hz), 7.27 (d, 2H, J=10.2 Hz), 7.40 (s, 1H), 7.45 (dd, 1H, J=1.8, 9.0 Hz), 7.54 (s, 1H), 7.60 (d, 2H, J=8.8 Hz), 8.62 (s, 2H); EI/MS 467 m/e (M$^+$); Anal. Calcd. for C$_{22}$H$_{15}$Cl$_2$F$_3$N$_2$O$_2$: C, 56.55; H, 3.24; N, 6.00. Found: C, 56.44; H, 3.37; N 5.90.

Example 9

Preparation of 4-[4-(4'-Iodophenyl)-5-methyl-4,5-dihydro-oxazol-2-yl]-3,5-dichloropyridines (Compounds 45 & 46)

N-[2-Hydroxy-1-(4-iodophenyl)-propyl]-2,5-dichloroisonicotinamide

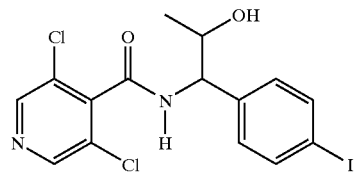

Lithium-3,5-dichloropyridine-4-carboxylate (0.54 g, 2.7 mmol) was suspended in 1,2-dichloroethane (10 mL). Thionyl chloride (0.42 mL, 5.7 mmol) and dimethylformamide (3 drops from a Pasteur pipette) were added. After refluxing under nitrogen for 5.5 hours, the reaction mixture was cooled to room temperature and concentrated under reduced pressure. 1,2-Dichloroethane (20 mL) was added to the residue and re-concentrated under reduced pressure. The brown residue was taken up in dry tetrahydrofuran (2.5 mL) and added to a suspension of 1-amino-2-hydroxy-1-(4-iodophenyl)propane hydrochloride (0.85 g, 2.7 mmol) in dry tetrahydrofuran (5 mL) at −5° C. The addition rate was controlled to keep reaction temperature at 0° C. The reaction mixture was stirred at room temperature for 14 hours. Methylene chloride (20 mL) and water (20 mL) were added to the reaction mixture and the organic layer was collected. The aqueous layer was extracted with more methylene chloride (2×10 mL). Combined organic extracts were washed with water (50 mL) and brine (30 mL), dried over magnesium sulfate, adsorbed on to silica, applied to a Michel-Miller column and eluted with 2:1 hexane/ethyl acetate. The major fraction was collected and concentrated under reduced pressure to leave 0.94 g (76%) of white solid: mp 210–213° C.; $^1$H NMR (DMSO-d$_6$) δ 9.32 (dd, 1H)*, 8.68 (s, 2H), 7.68 (d, 2H), 7.19 (dd, 2H), 4.71–4.95 (m, 2H)**, 3.91 & 3.80 (m, 1H), 1.13 (m, 3H). MI=451. IR (KBr) cm$^{-1}$ 3282 & 1654.

\* Signal disappeared upon shaking with D$_2$O
\*\* Signal collapsed into 2 doublets integrating to 1H upon D$_2$O shake 4-[4-(4'-Iodophenyl)-5-methyl-4,5-dihydro-oxazol-2-yl]-3,5-dichloropyridines (Compounds 45 & 46)

Compound 45

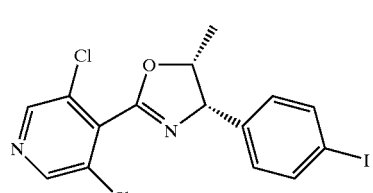

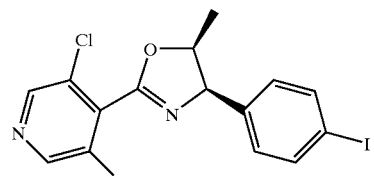

Compound 46

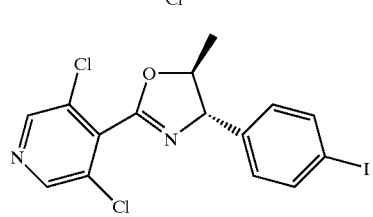

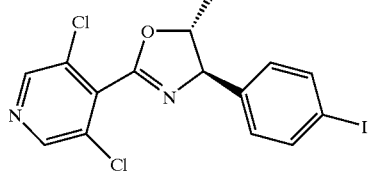

N-[2-Hydroxy-1-(4-iodophenyl)-propyl]-2,5-dichloroisonicotinamide (918 mg, 2 mmol) was dissolved in methylene chloride (220 mL) and cooled to −78° C. To this cloudy suspension was added (diethylamino)sulphur trifluoride (0.33 g, 2 mmol) at a dropwise rate over 10 minutes. The reaction mixture was allowed to come to room temperature overnight and poured into crushed ice (80 g) containing ammonia solution (10 mL). The organic layer was collected and the aqueous layer was extracted with methylene chloride (2×50 mL). Combined organic layers were washed with water (150 mL) and brine (100 mL), dried over magnesium sulfate, adsorbed onto silica, applied to a Michel-Miller column and eluted with, a gradient of ethyl acetate in hexane. Two pure fractions and one fraction containing a mixture of both compounds were collected and concentrated under reduced pressure. The faster moving fraction was shown by $^1$H NMR to contain the anti diastereomers. $^1$H NMR (CDCl$_3$) δ 8.60 (s, 2H), 7.73 (d, 2H), 7.12 (d, 2H), 4.92 (d, 2H), 4.67 (p, 1H), 1.61 (d, 3H); MI=433; mp 117–119° C. The total yield of this material was estimated by NMR to be 0.11 g (12%). The slower moving fraction was shown by $^1$H NMR to contain the syn diastereomers. $^1$H NMR (CDCl$_3$) δ 8.60 (s, 2H), 7.71 (d, 2H), 7.12 (d, 2H), 5.56 (d, 1H), 5.19–5.30 (m, 1H), 0.99 (t, 1H); MI=432; mp 99–100° C. The yield of this material was estimated by NMR to be 0.28 g (27%).

Example 10

Preparation of 4-[5-Methyl-4-(4'-trifluoromethoxybiphenyl)-4-yl)-4,5-dihydro-oxazol-2-yl]-3,5-dichloropyridines (Compounds 47 & 48)

Compound 47

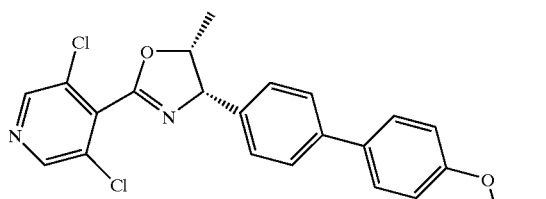

Compound 48

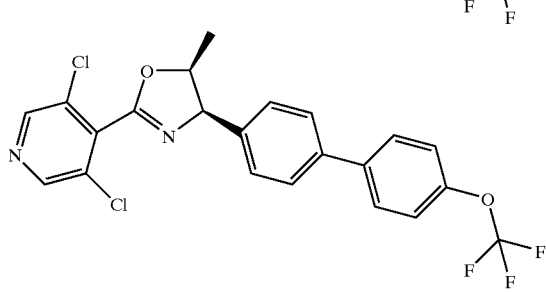

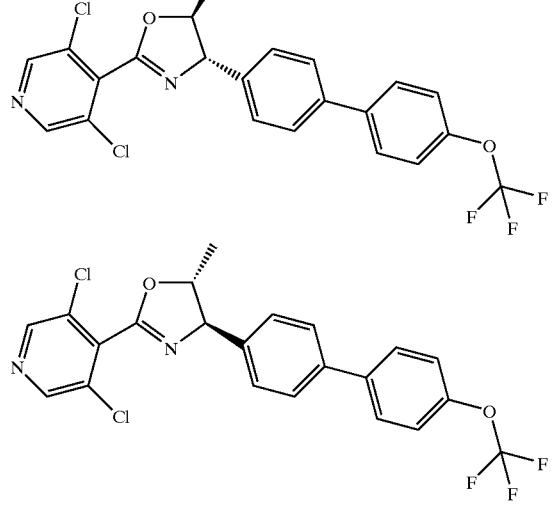

4-[4-(4'-Iodophenyl)-5-methyl-4,5-dihydro-oxazol-2-yl]-3,5-dichloropyridines (50/50 mixture, 200 mg, 0.5 mmol), 4-(trifluoromethoxy)-benzeneboronic acid (95 mg, 0.5 mmol), sodium carbonate (88 mg, 0.8 mmol), tri-o-tolylphosphine (14 mg, 45 nmol) and dichlorobis(triphenylphosphine)-palladium(II) (32 mg, 45 nmol) were combined in acetonitrile (5 mL). Water (0.5 mL) was added and the mixture refluxed under nitrogen for 5 hours. After cooling to room temperature, the mixture was poured into dilute hydrochloric acid (1N, 12 mL) and extracted with ether (3×15 mL). Combined ethereal extracts were washed with water (70 mL) and brine (70 mL), dried over magnesium sulphate, adsorbed onto silica, applied to a Michel-Miller column and eluted with 10:1 hexane/ethyl acetate. Two fractions were collected and concentrated under reduced pressure. The faster moving fraction was shown by $^1$H NMR to contain the anti diastereomers. $^1$H NMR (CDCl$_3$) δ 8.61 (s, 2H), 7.61 (d, 2H), 7.58 (d, 2H), 7.46 (d, 2H), 7.28 (d, 2H), 5.02 (d, 2H), 4.77 (p, 1H), 1.65 (d, 3H); MI=466; mp 132–133° C.; Yield of brown powder 34 mg (31%). The slower moving fraction was shown by $^1$H NMR to contain the syn diastereomers. $^1$H NMR (CDCl$_3$) δ 8.61 (s, 2H), 7.61 (d, 2H), 7.57 (d, 2H), 7.42 (d, 2H), 7.28 (d, 2H), 5.66 (d, 1H), 5.29 (m, 1H), 1.05 (d, 3H); MI=466; mp=147–148° C.; Yield of white powder 36 mg (33%).

Phytologically acceptable acid addition salts of the compounds of formula (I) are also within the scope of the invention. For example, boron tetrafluoride, hydrogen chloride, hydrogen bromide, hydrogen iodide, hydrogen sulfate, or organic acid salts may be used.

The compounds identified in the following Tables were prepared using the procedures illustrated in the foregoing examples, and the compounds were tested against tobacco budworm (TBW), beet armyworm (BAW), cabbage looper (CL), cotton aphid (CA), two-spotted spider mite (SM), and sweetpotato whitefly (WF) using procedures described hereinafter.

TABLE 1
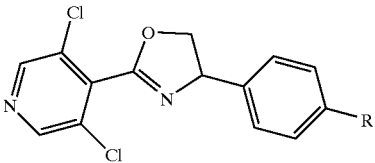
| compound number | R | mp °C. | TBW | BAW | CL | CA | SM | WF |
|---|---|---|---|---|---|---|---|---|
| 1 | —H | oil | — | — | — | F | G | F |
| 2 | —Cl | oil | G | G | G | A | F | F |
| 3 | —F | 93–95 | G | G | G | B | G | B |
| 4 | —Br | 102–103 | G | G | G | A | A | — |
| 5 | 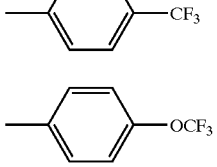 | 144–146 | F | A | A | B | A | F |
| 6 | 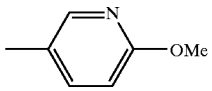 | 113–115 | G | A | A | A | A | F |
| 7 | 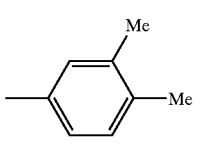 | 145–147 | G | D | B | G | A | — |
| 8 | 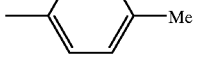 | 112–115 | G | A | B | B | — | — |
| 9 | 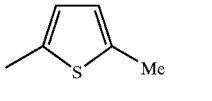 | 107–110 | G | A | G | A | G | G |
| 10 | 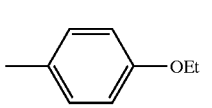 | 128–136 | G | B | A | D | G | G |
| 11 | —I | 90–92 | G | G | G | A | A | A |
| 12 | 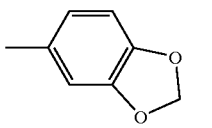 | 121–122 | B | A | D | B | A | B |
| 13 | 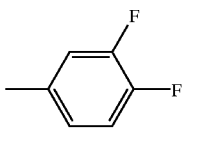 | 109–110 | G | D | A | B | F | G |
| 14 | 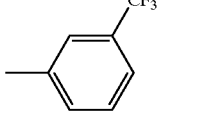 | 130 | G | B | G | D | A | G |
| 15 |  | oil | G | A | A | F | F | G |

TABLE 1-continued
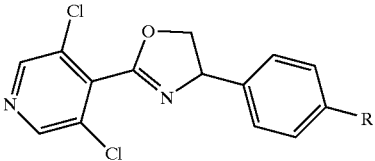
| compound number | R | mp °C. | TBW | BAW | CL | CA | SM | WF |
|---|---|---|---|---|---|---|---|---|
| 16 | 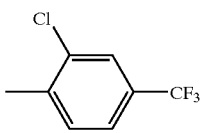 | 153–157 | D | A | A | F | A | G |
| 17 | 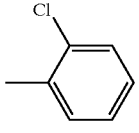 | gum | G | A | A | D | A | F |
| 18 | 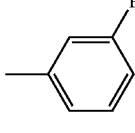 | oil | G | G | B | E | F | G |
| 19 | 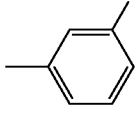 | 98–103 | G | G | D | F | A | F |
| 20 | 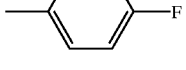 | oil | G | G | A | F | G | G |
| 21 | 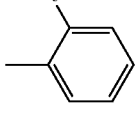 | 146–149 | G | B | G | A | A | F |
| 22 | 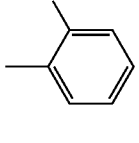 | 97–98 | G | G | G | C | G | G |
| 23 | 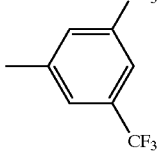 | 91–93 | G | D | A | A | A | G |
| 24 |  | foam | G | A | G | F | G | F |

TABLE 1-continued
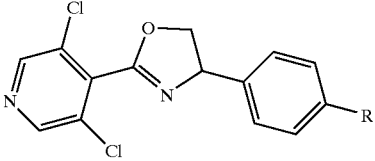
| compound number | R | mp °C. | TBW | BAW | CL | CA | SM | WF |
|---|---|---|---|---|---|---|---|---|
| 25 | 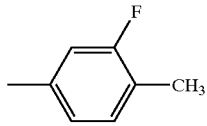 | 78–81 | G | A | F | B | G | G |
| 26 | 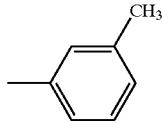 | 88–91 | G | D | D | D | G | G |
| 27 | 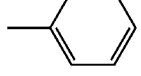 | 84–87 | F | A | A | A | B | G |
| 28 | 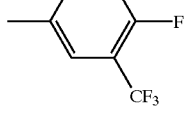 | 141–143 | G | B | G | F | A | G |
| 29 | 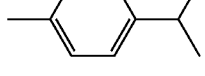 | oil | B | B | A | F | C | G |
| 30 | 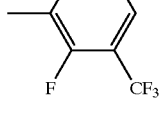 | 123–128 | G | A | D | F | C | F |
| 31 | 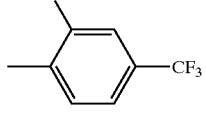 | 98–99 | D | G | G | G | F | G |
| 32 | 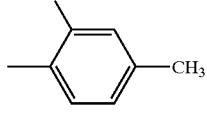 | oil | A | A | G | C | A | A |
| 33 |  | oil | G | B | G | F | G | G |

TABLE 1-continued
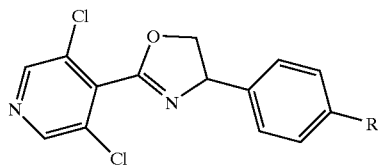
| compound number | R | mp °C. | TBW | BAW | CL | CA | SM | WF |
|---|---|---|---|---|---|---|---|---|
| 34 | 4-F, 3-CF₃ phenyl | oil | G | D | A | B | G | G |
| 35 | 4-SCH₃ phenyl | 170–173 | G | A | A | F | G | G |
| 36 | 4-S(O)CH₃ phenyl | 153–156 | D | G | A | F | G | F |
| 37 | 4-SCH₂F phenyl | 135–138 | G | G | D | A | F | G |
TABLE 2
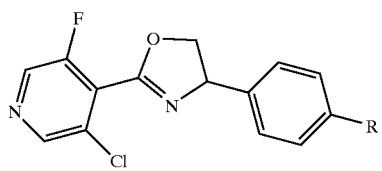
| compound number | R | mp °C. | TBW | BAW | CL | CA | SM | WF |
|---|---|---|---|---|---|---|---|---|
| 38 | —I | 84–86 | G | C | G | F | A | A |
| 39 | 4-CF₃ phenyl | 136–138 | G | B | A | F | A | F |
| 40 | 4-OCF₃ phenyl | 92–95 | G | A | A | F | A | G |

TABLE 3
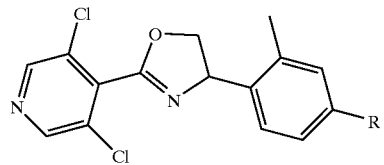
| compound number | R | mp °C. | TBW | BAW | CL | CA | SM | WF |
|---|---|---|---|---|---|---|---|---|
| 41 | —Br | 93–95 | G | G | G | A | F | F |
| 42 | —⟨⟩—OEt | 127–129 | G | A | B | B | A | G |
| 43 | —⟨⟩—CF₃ | 129–131 | A | A | A | B | B | F |
| 44 | —⟨⟩—OCF₃ | 100–102 | A | A | A | B | A | E |
TABLE 4
Compound #45
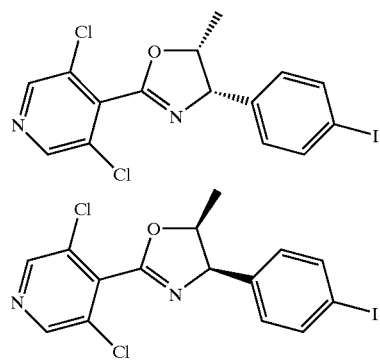
Compound #46
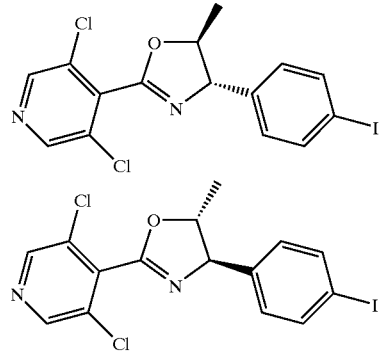
Compound #47
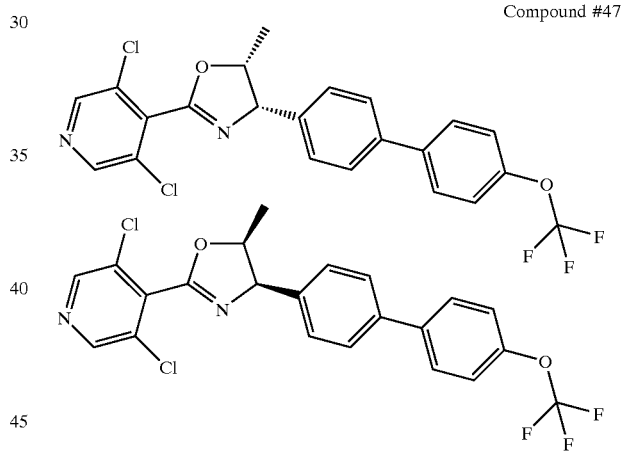
Compound #48
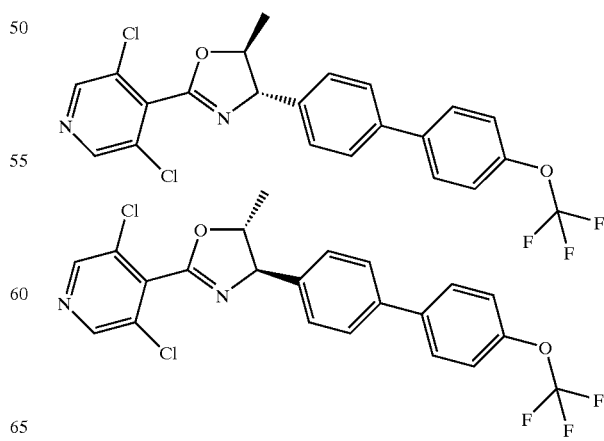

| compound number | mp ° C. | TBW | BAW | CL | CA | SM | WF |
|---|---|---|---|---|---|---|---|
| 45 | 99–100 | | | | A | | |
| 46 | 117–119 | G | G | G | F | F | G |
| 47 | 147–148 | A | A | A | A | A | G |
| 48 | 132–133 | A | G | A | B | E | F |

TBW refers to activity at 400 ppm against tobacco budworm,
BAW refers to activity at 400 ppm against beet armyworm,
CL refers to activity at 400 ppm against cabbage looper,
CA refers to activity at 50 ppm against cotton aphid,
SM refers to activity at 2.5 ppm against two-spotted spider mite,
WF refers to activity at 200 ppm against whitefly, In each case the rating scale is as follows

| % Control | Rating |
|---|---|
| 90–100 | A |
| 80–89 | B |
| 70–79 | C |
| 60–69 | D |
| 50–59 | E |
| less than 50 | F |
| Inactive | G |

Insecticide and Miticide Utility

The compounds of the invention are useful for the control of insects, mites, and aphids. Therefore, the present invention also is directed to a method for inhibiting an insect, mite, or aphid which comprises applying to a locus of the insect or mite an insect- or mite-inhibiting amount of a compound of formula (I).

The compounds are useful for reducing populations of insects and mites and are useful in a method of inhibiting an insect or mite population which comprises applying to a locus of the insect or mite an effective insect- or mite-inactivating amount of a compound of formula (I). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts that the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites, or a decrease in the number of viable insect or mite eggs. The extent of reduction accomplished by a compound depends, of course, upon the application rate of the compound, the particular compound used, and the target insect or mite species. At least an inactivating amount should be used. The terms "insect-inactivating amount" and "mite-inactivating amount" are used to describe the amount, which is sufficient to cause a measurable reduction in the treated insect or mite, population. Generally an amount in the range from about 1 to about 1000 ppm by weight active compound is used.

In a preferred embodiment, the present invention is directed to a method for inhibiting a mite or aphid which comprises applying to a plant an effective mite- or aphid-inactivating amount of a compound of formula (I).

Insecticidal Test for Tobacco Budworm (*Heliothis virescens*), Beet Armyworm (*Spodoptera exigua*), and Cabbage Looper (*Trichoplusia ni*).

To prepare the test solution, the test compound was formulated at 400 ppm in 7.5 mL of 2 acetone:1 tap water. 250 μL of the test solution was pipetted upon the surface of 8 mL of lepidopteran diet (modified Shorey) contained in each of five one-ounce plastic cups (one cup=1 replication). A second-instar beet armyworm was placed upon the treated diet in each cup once the solvent had air-dried. The solutions remaining after completing applications to the one-ounce cups were then used as leaf-dip solutions for 3.5 cm leaf discs cut from cabbage leaves and cotton cotyledons. Five discs of each type of plant were dipped until thoroughly coated into each rate of each compound (=5 replications of each treatment). After air-drying, the treated leaf discs were placed individually into one-ounce plastic cups. Each dried, treated cotton cotyledon disc was infested with a $2^{nd}$ instar tobacco budworm larva, and each cabbage leaf disc was infested with a $2^{nd}$ instar cabbage looper larva. Cups containing the treated substrates and larvae were capped and then held in a growth chamber at 25° C., 50–55% RH, and 14 hr light: 10 hr dark for 5 days. The number of dead insects of 5 per species per treatment was then determined and the results are given in Tables 1–4.

Insecticidal Test for Cotton Aphid (*Aphis gossypii*)

To prepare spray solutions, 1 mg of each test compound was dissolved into 1 mL of a 90:10 acetone:ethanol solvent. This 1 mL of chemical solution was added to 19 mL of water containing 0.05% Tween 20 surfactant to produce a 50 ppm spray solution.

Squash cotyledons were infested with cotton aphid (all life stages)16–20 hours prior to application of spray solution. The solution was sprayed on both sides of each infested squash cotyledon (0.5 mL×2 each side) with a sweeping action until runoff. The plants were allowed to air dry and held for 3 days in a controlled room at 26° C. and 40% RH after which time the test was graded. Grading was by actual count using a dissecting microscope and comparison of test counts to the untreated check. Results are given in Tables 1–4 as percent control based on population reduction versus the untreated.

Insecticidal Test for Two-Spotted Spider Mite (*Tetranychus urticae*)

Ovicide Method:

Ten adult female two-spotted spider mites were placed on eight 2.2 cm leaf discs of cotton leaf, allowed to oviposit over 24 hours, and thereafter removed. The leaf discs were sprayed with 100 ppm test solutions using a hand syringe, then allowed to dry with sixteen discs left untreated as a negative control. Discs were placed on an agar substrate and held at 24° C. and 90% RH for 6 days. Percent control based on the number of hatched larvae on treated discs and the number on untreated discs is reported in Tables 1–4.

Insecticidal Test for Sweetpotato Whitefly (*Bemisia tabacia*)

Four mg of each test compound was dissolved by adding 4 mL of a 90:10 acetone:ethanol solvent mixture to the vial containing the sample compound. This solution was added to 16 mL of water containing 0.05% Tween 20 surfactant to produce 20 mL of a 200 ppm spray solution.

Five-week-old cotton plants reared in a greenhouse were stripped of all foliage except for the two uppermost true leaves that were greater than 5 cm in diameter.

These plants were then placed into a laboratory colony of whiteflies for two days for oviposition by the colony females. All whiteflies were then removed from the test plants with pressurized air. The spray solution was then applied to the test plants with a hand-held syringe fitted with hollow cone nozzle. One mL of spray solution was applied to each leaf top and bottom for a total of 4 mL per plant. Four replications of each test compound utilized a total of 16 mL spray solution. Plants were air dried and then placed in a holding chamber (28° C. and 60% RH) for 13 days. Compound efficacy was evaluated by counting, under an illuminated magnifying glass, the number of large nymphs (3rd–4th instar) per leaf.

Percent control based on reduction of large nymphs of a test compound compared to solution-only (no test compound) sprayed plants is reported in Tables 1–4.

In addition to being effective against mites, aphids, and insects when applied to foliage, compounds of formula (I) have systemic activity. Accordingly, another aspect of the invention is a method of protecting a plant from insects which comprises treating plant seed prior to planting it, treating soil where plant seed is to be planted, or treating soil at the roots of a plant after it is planted, with an effective amount of a compound of formula (I).

Compositions

The compounds of this invention are applied in the form of compositions which are important embodiments of the invention, and which comprise a compound of this invention and a phytologically-acceptable inert carrier. The compositions are either concentrated formulations that are dispersed in water for application, or are dust or granular formulations that are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects, mites, and aphids is not critical and can readily be determined by those skilled in the art in view of the examples above. In general, concentrations of from 10 ppm to 5000 ppm by weight of compound are expected to provide good control. With many of the compounds, concentrations of from 100 to 1500 ppm will suffice. For field crops, such as soybeans and cotton, a suitable application rate for the compounds is about 0.5 to 1.5 lb/Acre, typically applied in 5–20 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grapevines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

We claim:

1. A compound of the formula (I)

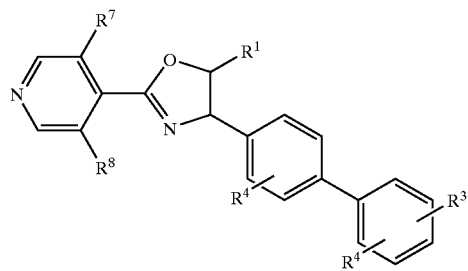

wherein $R^1$ represents H, $(C_1-C_6)$ alkyl, $(C_1-C_6)$ haloalkyl, $(C_2-C_6)$ alkenyl, $(C_2-C_6)$ alkynyl, or $(C_1-C_6)$ alkoxyalkyl;

$R^3$ represents H, halogen, $(C_1-C_6)$ alkyl, $(C_7-C_{21})$ straight chain alkyl, hydroxy, $(C_1-C_6)$ alkoxy, $(C_1-C_6)$ haloalkyl, $(C_1-C_6)$ haloalkoxy, $(C_1-C_6)$ alkoxyalkyl, $(C_1-C_6)$ alkoxyalkoxy, $(C_2-C_6)$ alkenyl, $(C_2-C_6)$ haloalkenyl, CN, $NO_2$, $CO_2R^6$, $CON(R^6)_2$, $(C_3-C_6)$ cycloalkyl, $S(O)_mR^6$, SCN, pyridyl, substituted pyridyl, isoxazolyl, substituted isoxazolyl, thienyl, substituted thienyl, thiazolyl, substituted thiazolyl, phenyl, substituted phenyl, $-(CH_2)_nR^6$, $-CH=CHR^6$, $-C\equiv CR^6$, $-CH_2OR^6$, $-CH_2SR^6$, $-CH_2NR^6R^6$, $-OCH_2R^6$, $-SCH_2R^6$, $-NR^6CH_2R^6$,

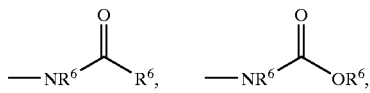

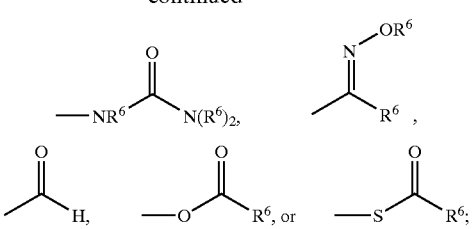

$R^4$ represents H, halogen, $(C_1-C_6)$ alkyl, $(C_1-C_6)$ alkoxy, $(C_1-C_6)$ haloalkyl, $(C_1-C_6)$ haloalkoxy, CN, $CO_2R^6$, $CON(R^6)_2$, $(C_1-C_6)$ $S(O)_m$ alkyl or $(C_1-C_6)$ $S(O)_m$ haloalkyl; $R^6$ is H, $(C_1-C_6)$ alkyl, $(C_1-C_6)$ haloalkyl, $(C_2-C_6)$ alkenyl, $(C_2-C_6)$ alkynyl, phenyl, or substituted phenyl;

$R^7$ and $R^8$ are independently Cl or F;

m is 0, 1, or 2; and n is 1 or 2;

or a phytologically-acceptable acid addition salt or N-oxide thereof or stereoisomers or mixtures thereof.

2. A compound of claim 1 in which $R^3$ and each $R^4$ independently represent H, halogen, $(C_1-C_6)$ alkyl, $(C_1-C_6)$ alkoxy, $(C_1-C_6)$ haloalkyl or $(C_1-C_6)$ haloalkoxy.

3. A compound of claim 1 in which $R^1$ represents H or methyl.

4. A compound of claim 3 in which $R^1$ represents methyl and the compound consists of individual stereoisomers or mixtures thereof.

5. A composition for controlling insects or mites which comprises a compound of claim 1 in combination with a phytologically-acceptable carrier.

* * * * *